(12) United States Patent
Hober et al.

(10) Patent No.: US 7,709,209 B2
(45) Date of Patent: May 4, 2010

(54) PROTEIN LIGANDS

(75) Inventors: Sophia Hober, Stockholm (SE); Hans J. Johansson, Uppsala (SE); Tomas Bjorkman, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 310 days.

(21) Appl. No.: 11/363,078

(22) Filed: Feb. 27, 2006

(65) Prior Publication Data

US 2006/0194955 A1    Aug. 31, 2006

Related U.S. Application Data

(63) Continuation-in-part of application No. 10/508,625, filed as application No. PCT/SE03/00475 on Mar. 20, 2003.

(30) Foreign Application Priority Data

Mar. 25, 2002   (SE)  .................... 0200943

(51) Int. Cl.
*C07K 16/18*   (2006.01)
(52) U.S. Cl. ..................... 435/7.1; 530/388.1
(58) Field of Classification Search .............. 435/7.1; 530/388.1
See application file for complete search history.

(56) References Cited

FOREIGN PATENT DOCUMENTS

WO    WO 00/23580    4/2000

OTHER PUBLICATIONS

Cedergren, L., et al., "Mutational analysis of the interaction between staphylococcal protein A and human IgG-1", *Protein Engineering*, vol. 6, 1993, p. 441-448.
Geiger, T., et al., "Deamidation, Isomerization, and Racemization at Asparaginyl and Aspartyl Residues in Peptides", *The Journal of Biological Chemistry*, vol. 262, Jan. 15, 1987 p. 785-794.
Gulich, S., et al., "Stability towards alkaline conditions can be engineered into a protein ligand", *Journal of Biotechnology*, vol. 80, 2000, p. 169-178.
Jendeberg, L., et al., "Kinetic analysis of the interaction between protein A domain variants and human Fc using plasmon resonance detection", *Journal of Molecular Recognition*, vol. 8, 1995, p. 270-278.
Karlstrom, A., et al., "Dual labeling of the binding protein allows for specific fluorescence detection of native protein", *Analytical Biochemistry*, vol. 295, Aug. 1, 2001, p. 22-30.
Nilsson, B., et al., "A synthetic IgG-binding domain based on staphylococcal protein A", *Protein Engineering*, vol. 1, 1987, p. 107-113.

*Primary Examiner*—Lynn Bristol
(74) *Attorney, Agent, or Firm*—Yonggang Ji

(57) ABSTRACT

The present invention relates to the use of an alkali-stable protein, wherein at least one asparagine residue has been mutated to an amino acid other than glutamine or aspartic acid, which mutation confers an increased chemical stability at pH-values of up to about 13-14 compared to the parental molecule. The protein can for example be derived from a protein capable of binding to other regions of the immunoglobulin molecule than the complementarity determining regions (CDR), such as protein A, and preferably the B-domain of Staphylococcal protein A. The invention also relates to a matrix for affinity separation, which comprises an immunoglobulin-binding protein as ligand coupled to a solid support, in which protein ligand at least one asparagine residue has been mutated to an amino acid other than glutamine.

5 Claims, 12 Drawing Sheets

FIG. 3

```
        KpnI       AccI
        ~~~~~~     ~~~~~~
    L    G    T    V    D    A*   K    F    D*   K    E    Q    N    A    F    Y    E    I    L
    CTG  GGT  ACC  GTA  GAC  GCC  AAA  TTC  GAC  AAA  GAA  CAA  AAC  GCG  TTC  TAT  GAG  ATC  TTA
    GAC  CCA  TGG  CAT  CTG  CGG  TTT  AAG  CTG  TTT  CTT  GTT  TTG  CGC  AAG  ATA  CTC  TAG  AAT

H    L    P    N    L    T*   E    E    Q    R    N    A    F    I    Q    S    L    K    D
    CAT  TTA  CCT  AAC  TTA  ACT  GAA  GAA  CAA  CGA  AAC  GCC  TTC  ATC  CAA  AGT  TTA  AAA  GAT
    GTA  AAT  GGA  TTG  AAT  TGA  CTT  CTT  GTT  GCT  TTG  CGG  AAG  TAG  GTT  TCA  AAT  TTT  CTA

P    S    Q    A    N    L    A    E    A    K    K    L    N    D    A    Q    A    P
    CCA  AGC  CAA  GCT  AAC  CTT  TTA  GCA  GAA  AAA  AAG  CTA  AAT  GAT  GCT  CAG  GCG  CCG
    GGT  TCG  GTT  CGA  TTG  GAA  AAT  CGT  CTT  TTT  TTC  GAT  TTA  CTA  CGA  GTC  CGC  GGC

PstI
        ~~~~~~
         L    Q    L
    K    C    .
    AAA  TGC  TAA  CTG  CAG  CTC
    TTT  ACG  ATT  GAC  GTC  GAG
```

FIG. 5

```
        AccI
        ~~~~~~
         V   D   A*  K   F   D*  K   E   Q   Q   N   A   F   Y   E   I   L
TTT TTT GTA GAC GCC AAA TTC GAC AAA GAA CAA CAA AAC GCG TTC TAT GAG ATC TTA
AAA AAA CAT CTG CGG TTT AAG CTG TTT CTT GTT GTT TTG CGC AAG ATA CTC TAG AAT

H   L   P   N   L   T*  E   E   Q   A   R   N   A   F   I   Q   S   L   K   D   D
CAT TTA CCT AAC TTA ACT GAA GAA CAA CGA AAC GCC TTC ATC CAA AGT TTA AAA GAT GAC
GTA AAT GGA TTG AAT TGA CTT CTT GTT GCT TTG CGG AAG TAG GTT TCA AAT TTT CTA CTG

P   S   Q   S   A   N   L   A   E   A   K   K   L   N   D   A   Q   A   P
CCA AGC CAA AGC GCT AAC CTT TTA GCA GAA GCT AAA AAG CTA AAT GAT GCT CAG GCG CCG
GGT TCG GTT TCG CGA TTG GAA AAT CGT CTT CGA TTT TTC GAT TTA CTA CGA GTC CGC GGC

AccI
        ~~~~~~
 K
AAA GTA GAC AAA AAA
TTT CAT CTG TTT TTT
```

FIG. 7
```
AFFI-88:    PO3^2- -GCA GGG TAC CCT GCA
AFFI-89:         GGG TAC CCT GC
```
$$PO_3^{2-}-\text{GCAGGGTACC CTGCA}$$
$$\text{CGTCCCATGG G}$$
(KpnI site indicated above GGGTACC)
FIG. 8
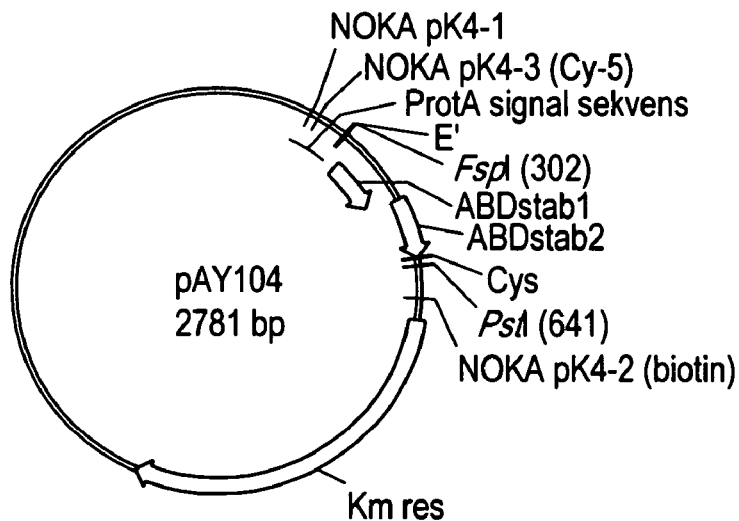
FIG. 9
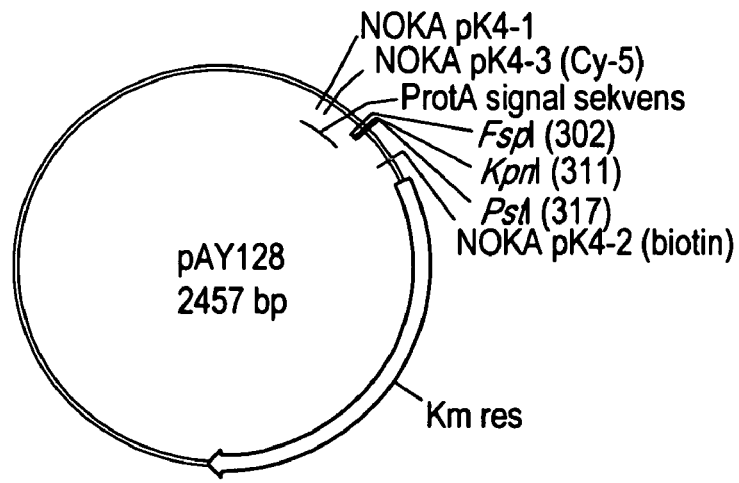

FIG. 10

```
                KpnI
               ~~~~~~
    FspI                  PstI
    ~~ ~~~               ~~~~~~
...GCAAATGCTG CGCAGGGTAC CCTGCAGGGG GGGGGGGGAA...
...CGTTTACGAC GCGTCCCATG GGACGTCCCC CCCCCCCCTT...
```

FIG. 11

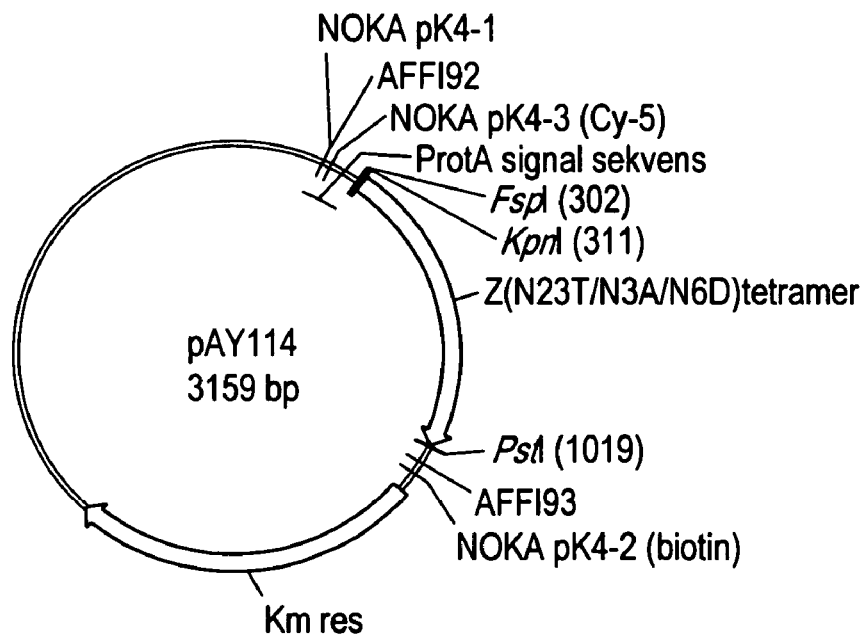

FIG. 12

```
AFFI-90:   PO3^2- -GCA ACA CGA TGA AGC CGG TAC CCT GCA
AFFI-91:          · GGG TAC CGG CTT CAT CGT GTT GC

KpnI
                       ~~~~~~
    FspI                         PstI
    ~~ ~~~~                     ~~~~~~
...GCAAATGCTG CGCAACACGA TGAAGCCGGT ACCCTGCAGG GGGGGGGGGG...
...CGTTTACGAC GCGTTGTGCT ACTTCGGCCA TGGGACGTCC CCCCCCCCCC...
```

Alkaline stability

PROTEIN LIGANDS

CROSS-REFERENCE TO RELATED APPLICATIONS

This application is a continuation-in-part of U.S. patent application Ser. No. 10/508,625 filed Sep. 20, 2004, which is a filing under 37 U.S.C. §371 and claims priority to international patent application number PCT/SE03/00475 filed Mar. 20, 2003, published on Oct. 2, 2003 as WO03/080655 and also claims priority to patent application number 0200943-9 filed in Sweden on Mar. 25, 2002; the disclosures of which are incorporated herein by reference in their entireties.

TECHNICAL FIELD

The present invention relates to the field of mutant proteins, and more specifically to a mutant protein that exhibits improved stability compared to the parental molecule as well as to a method of producing a mutant protein according to the invention. The invention also relates to an affinity separation matrix, wherein a mutant protein according to the invention is used as an affinity ligand.

BACKGROUND OF THE INVENTION

A great number of applications in the biotechnological and pharmaceutical industry require comprehensive attention to definite removal of contaminants. Such contaminants can for example be non-eluted molecules adsorbed to the stationary phase or matrix in a chromatographic procedure, such as non-desired biomolecules or microorganisms, including for example proteins, carbohydrates, lipids, bacteria and viruses. The removal of such contaminants from the matrix is usually performed after a first elution of the desired product in order to regenerate the matrix before subsequent use. Such removal usually involves a procedure known as cleaning-in-place (CIP), wherein agents capable of eluting contaminants from the stationary phase are used. One such class of agents often used is alkaline solutions that are passed over said stationary phase. At present the most extensively used cleaning and sanitising agent is NaOH, and the concentration thereof can range from 0.1 up to e.g. 1 M, depending on the degree and nature of contamination. NaOH is known to be an effective CIP agent achieving multilog reduction of contaminants, such as microbes, proteins, lipids and nucleic acids. Another advantage of NaOH is that it can easily be disposed of without any further treatment. However, this strategy is associated with exposing the matrix for pH-values above 13. For many affinity chromatography matrices containing proteinaceous affinity ligands such alkaline environment is a very harsh condition and consequently results in decreased capacities owing to instability of the ligand to the high pH involved.

An extensive research has therefore been focussed on the development of engineered protein ligands that exhibit an improved capacity to withstand alkaline pH-values. For example, Gülich et al (Susanne Gülich, Martin Linhult, Per-Åke Nygren, Mathias Uhlén, Sophia Hober, Journal of Biotechnology 80 (2000), 169-178: Stability towards alkaline conditions can be engineered into a protein ligand) suggested protein engineering to improve the stability properties of a Streptococcal albumin-binding domain (ABD) in alkaline environments. Previously, it was shown that structural modification, such as deamidation and cleavage of the peptide backbone, of asparagine and glutamine residues in alkaline conditions is the main reason for loss of activity upon treatment in alkaline solutions, and that asparagine is the most sensitive of the two (Geiger, T., and S. Clarke. 1987. Deamidation, Isomerization, and Racemization at Asparaginyl and Aspartyl Residues in Peptides. *J. Biol. Chem.* 262:785-794). It is also known that the deamidation rate is highly specific and conformation dependent (Kosky, A. A., U. O. Razzaq, M. J. Treuheit, and D. N. Brems. 1999. The effects of alpha-helix on the stability of Asn residues: deamidation rates in peptides of varying helicity. *Protein Sci.* 8:2519-2523; Kossiakoff, A. A. 1988. Tertiary structure is a principal determinant to protein deamidation. *Science.* 240:191-194; and Lura, R., and V. Schirch. 1988. Role of peptide conformation in the rate and mechanism of deamidation of asparaginyl residues. *Biochemistry.* 27:7671-7677), and the shortest deamidation half times have been associated with the sequences asparagine-glycine- and -asparagine-serine. Accordingly, Gülich et al created a mutant of ABD, wherein all the four asparagine residues of native ABD have been replaced by leucine (one residue), asparte (two residues) and lysine (one residue). Further, Gülich et al report that their mutant exhibits a target protein binding behaviour similar to that of the native protein, and that affinity columns containing the engineered ligand show higher binding capacities after repeated exposure to alkaline conditions than columns prepared using the parental non-engineered ligand. Thus, it is concluded therein that all four asparagine residues can be replaced without any significant effect on structure and function.

Thus, the studies performed by Gülich et al were performed on a Streptococcal albumin-binding domain. However, affinity chromatography is also used in protocols for purification of other molecules, such as immunoglobulins, e.g. for pharmaceutical applications. A particularly interesting class of affinity reagents is proteins capable of specific binding to invariable parts of an antibody molecule, such interaction being independent on the antigen-binding specificity of the antibody. Such reagents can be widely used for affinity chromatography recovery of immunoglobulins from different samples such as but not limited to serum or plasma preparations or cell culture derived feed stocks. An example of such a protein is staphylococcal protein A, containing domains capable of binding to the Fc and Fab portions of IgG immunoglobulins from different species.

Staphylococcal protein A (SpA) based reagents have due to their high affinity and selectivity found a widespread use in the field of biotechnology, e.g. in affinity chromatography for capture and purification of antibodies as well as for detection. At present, SpA-based affinity medium probably is the most widely used affinity medium for isolation of monoclonal antibodies and their fragments from different samples including industrial feed stocks from cell cultures. Accordingly, various matrices comprising protein A-ligands are commercially available, for example, in the form of native protein A (e.g. Protein A SEPHAROSE™, Amersham Biosciences, Uppsala, Sweden) and also comprised of recombinant protein A (e.g. rProtein A SEPHAROSE™, Amersham Biosciences, Uppsala, Sweden). More specifically, the genetic manipulation performed in said commercial recombinant protein A product is aimed at facilitating the attachment thereof to a support.

Accordingly, there is a need in this field to obtain protein ligands capable of binding immunoglobulins, especially via the Fc-fragments thereof, which are also tolerant to one or more cleaning procedures using alkaline agents.

In addition, it is well known that the cell culture supernatants from which recombinant proteins and immunoglobulins are commonly purified usually contain a variety of enzymes, some of which may harm a sensitive protein-based ligand. As is easily realised, one potentially detrimental group of enzymes to protein-based ligands is proteases which break their peptide bonds and consequently degrade the ligands. In fact, ligand leakage is a well known problem in affinity chromatography.

U.S. Pat. No. 5,429,746 (Smithkline Beecham) relates to antibody purification, and more specifically to the purification of an IgG antibody from conditioned cell culture medium containing same comprising sequentially subjecting the medium to (a) Protein A, (b) ion exchange chromatography, and (c) hydrophobic interaction chromatography. In another aspect, U.S. Pat. No. 5,429,746 provides a method for removing Protein A from a mixture comprising Protein A and antibodies comprising contacting said mixture with a hydrophobic interaction chromatography support and selectively eluting the antibody from the support. Thus, according to the teachings of U.S. Pat. No. 5,429,746, leaked Protein A can be removed from the eluent by adding one or two additional chromatography steps.

Accordingly, in order to improve process economy, there is still a need in this field of reducing ligand leakage in antibody processes.

BRIEF SUMMARY OF THE INVENTION

One object of the present invention is to reduce ligand leakage from protein-based chromatography ligands in a process for antibody purification. This can be achieved by reducing or substantially eliminating the binding of enzymes such as proteases to the ligands, which will result in shorter contact time between ligand and enzyme and consequently a reduced leakage of ligand.

Another object of the present invention is to provide a method for purification of immunoglobulins, wherein the contact time between the immunoglobulins and enzymes such as proteases is reduced as compared to the prior art methods.

A specific object of the invention is to provide such as method, wherein the immunoglobulins are adsorbed to an affinity adsorbent while the proteases remain in the liquid without being adsorbed.

One object of the present invention is to provide a mutated immunoglobulin-binding protein ligand that exhibits an improved stability at increased pH-values, and accordingly an improved tolerance to cleaning under alkaline conditions, as compared to the parental molecule.

Another object of the invention is to provide such a protein ligand, which binds specifically to the Fc-fragment of immunoglobulins, such as IgG, IgA and/or IgM.

Yet another object of the invention is to provide a protein ligand as described above, which also exhibits an affinity which is retained for a longer period of time in alkaline conditions than that of the parental molecule.

A further object of the present invention is to provide an affinity separation matrix, which comprises mutant protein ligands capable of binding immunoglobulins, such as IgG, IgA and/or IgM, preferably via their Fc-fragments, which ligands exhibit an improved tolerance to cleaning under alkaline conditions, as compared to the parental molecule ligand.

One or more of the above-defined objects can be achieved as described in the appended claims.

DETAILED DESCRIPTION OF THE DRAWINGS

FIG. 1 (SEQ ID NOs: 5-9, 1 & 10-11, respectively, in order of appearance) shows amino acid alignments of the five homologous domains (E, D, A, B and C) of SpA. Horizontal lines indicate amino acid identity. The three boxes show the α-helices of $Z_{wt}$ as determined by Tashiro and co-workers (Tashiro et al., 1997). The asparagine residues, and also one glycine residue in the B domain, which were replaced, are underlined in the figure. Also, amino acid alignments for Zwt and Z(N23T) are shown.

FIG. 2 illustrates the results obtained after alkaline treatment (cleaning-in-place) of mutant proteins according to the invention as compared to the destabilised protein Z. A comparison of the capacity after repeated CIP-treatment following an ordinary affinity chromatography scheme. 0.5 M NaOH was used as cleaning agent. The protocol was run 16 times and the duration for the alkaline sanitisation was 30 minutes in each round. FIG. 2(a) shows the inactivation pattern for Z(F30A) and variants thereof, whereas FIG. 2(b) shows the inactivation pattern for Zwt and Z(N23T).

FIG. 3 (SEQ ID NOs: 12-13) shows the gene encoding the Z(N23T/N3A/N6D)-Cys after insertion into vector as described in example 4(a). The mutations are marked with *.

FIG. 5 (SEQ ID NOs: 14-15) shows the gene encoding the Z(N23T/N3A/N6D) after insertion into vector as described in example 4(b). The mutations are marked with *.

FIG. 7 (SEQ ID NOs: 16, 17 & 16, respectively, in order of appearance) shows the adapter for introducing a KpnI-site into a vector with SPA promoter and signal sequence according to example 6.

FIG. 8 shows the plasmid pAY104, which contains SPA promoter and signal sequence to be used for introduction of an adapter containing a KpnI-site, as described in example 6.

FIG. 9 shows the resulting plasmid, pAY128, after insertion of the adapter according to example 6.

FIG. 10 (SEQ ID NO: 18) shows the constructed cloning cassette of example 6, where the original adapter is underlined.

FIG. 11 shows plasmid pAY114 after insertion of the Z(N23T/N3A/N6D)-Cys-tetramer as described in Example 6.

FIG. 12 (SEQ ID NOs: 19-21, respectively, in order of appearance) shows the constructed cloning cassette of example 7, where the original adapter is underlined.

Figure 13:
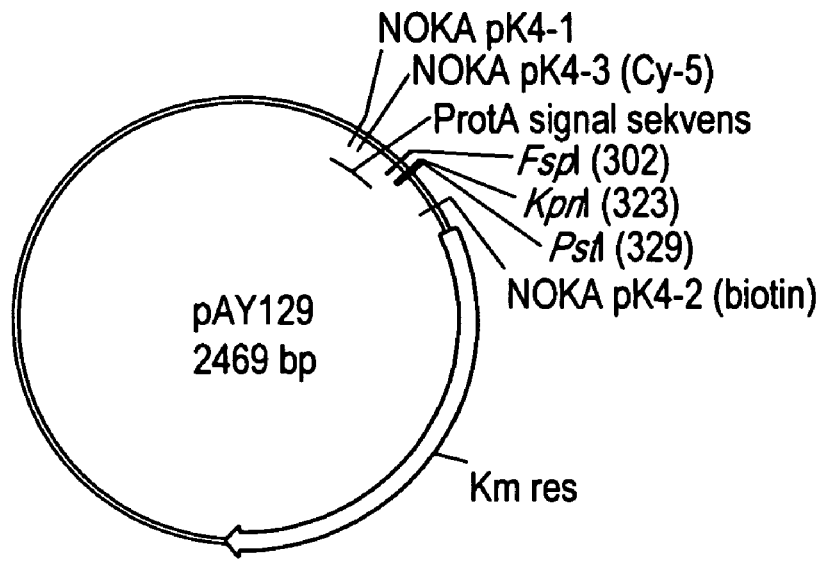

FIG. 13 shows the resulting plasmid, pAY129, after insertion of the adapter according to example 7.

Figure 14:
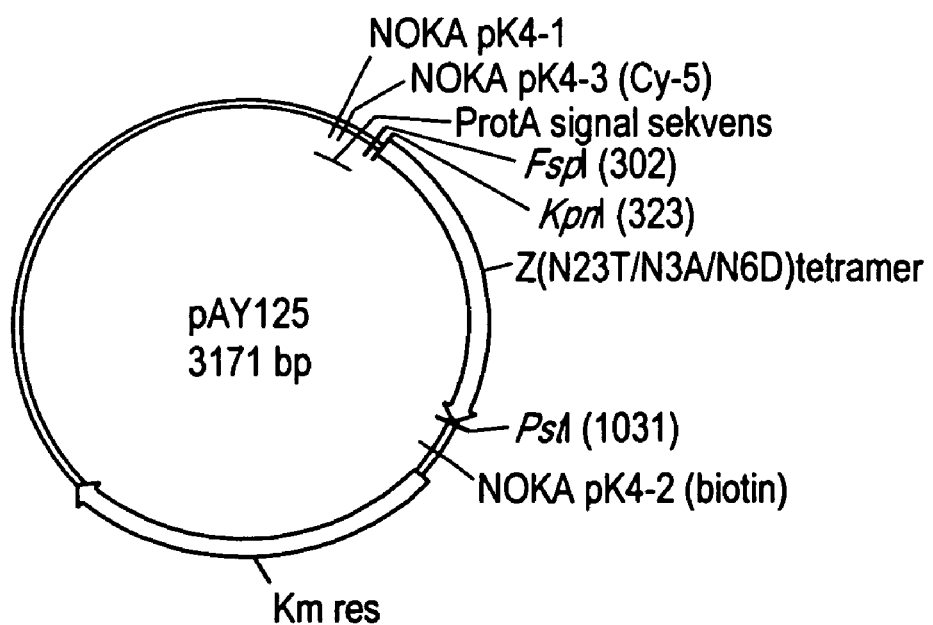

FIG. 14 shows plasmid pAY125 after insertion of the Z(N23T/N3A/N6D)tetramer-Cys as described in example 7.

Figure 15:
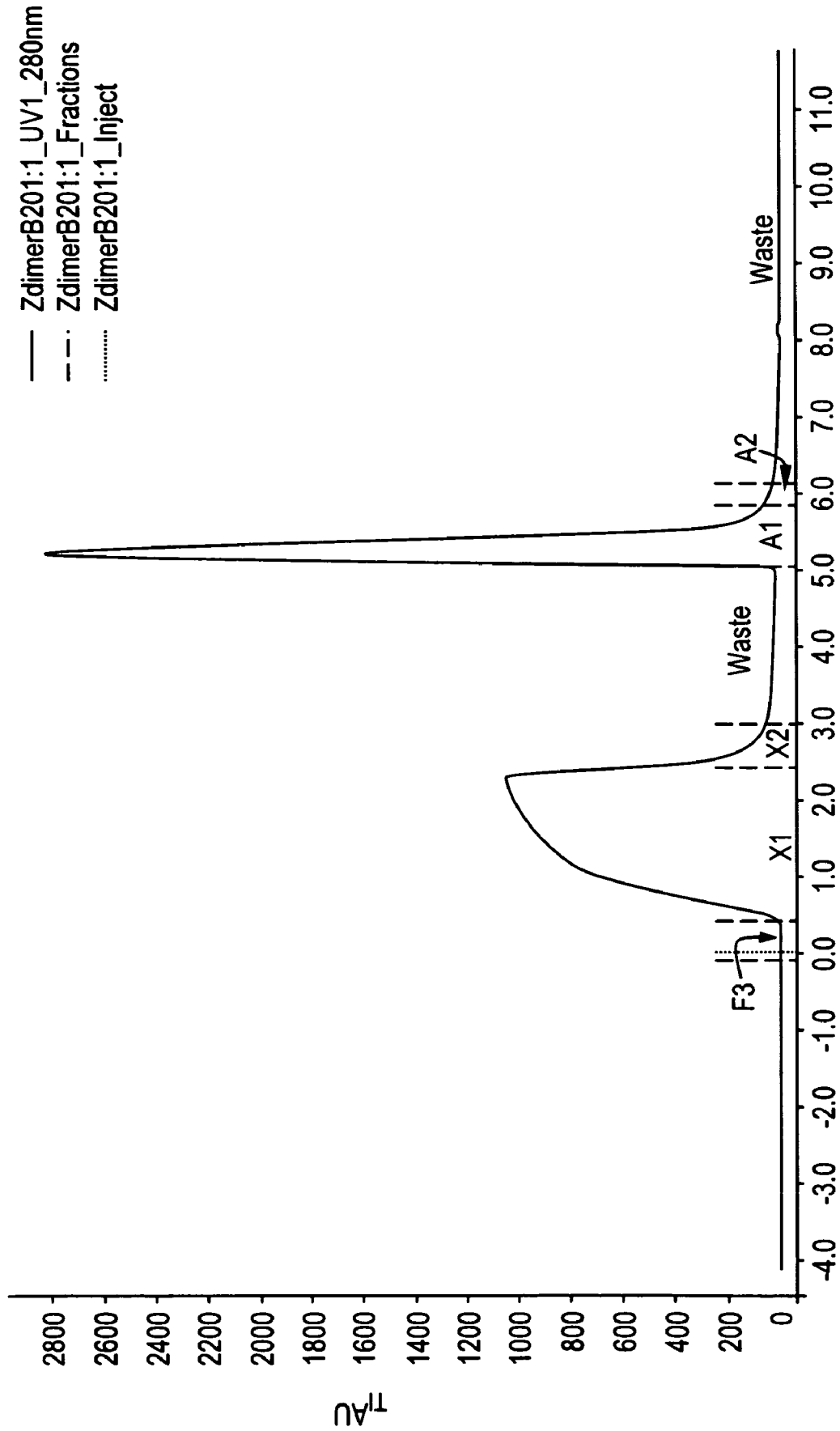

FIG. 15 is a chromatogram obtained from a run as described in example 8, where the first peak corresponds to the flow-through material and the second peak corresponds to eluted hIgG.

Figure 16:
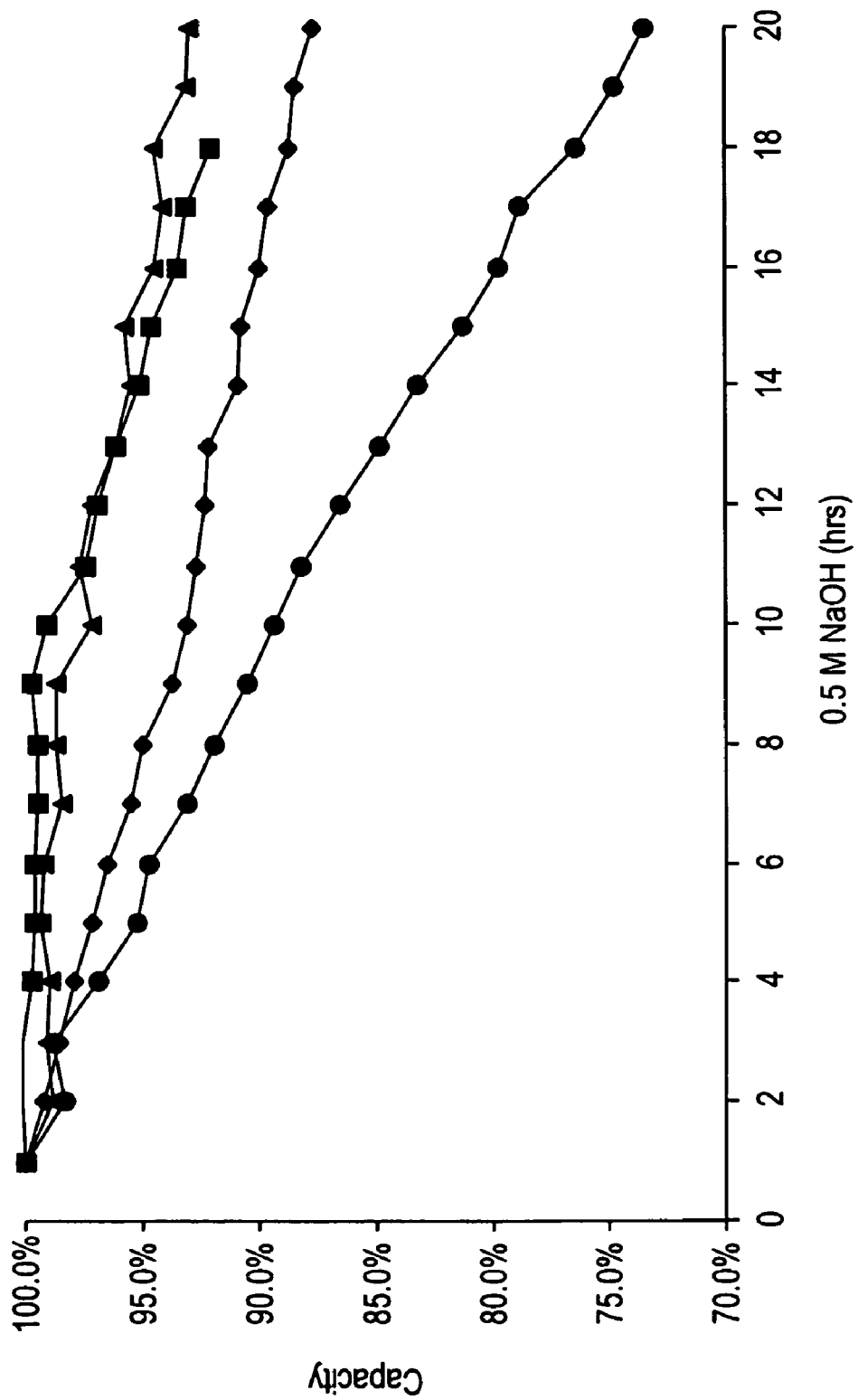

FIG. 16 shows graphs that represent the remaining dynamic binding capacity of the matrices in accordance with example 8. From top to bottom they represent Z(N23T/N3A/N6D)dimer-Cys, Z(N23T/N3A)dimer-Cys, Z(N23T)dimer-Cys and Z(N23T/K4G)dimer-Cys respectively. Due to software problems the last two measure points for Z(N23T/N3A) dimer-Cys are lacking.

Figure 17:
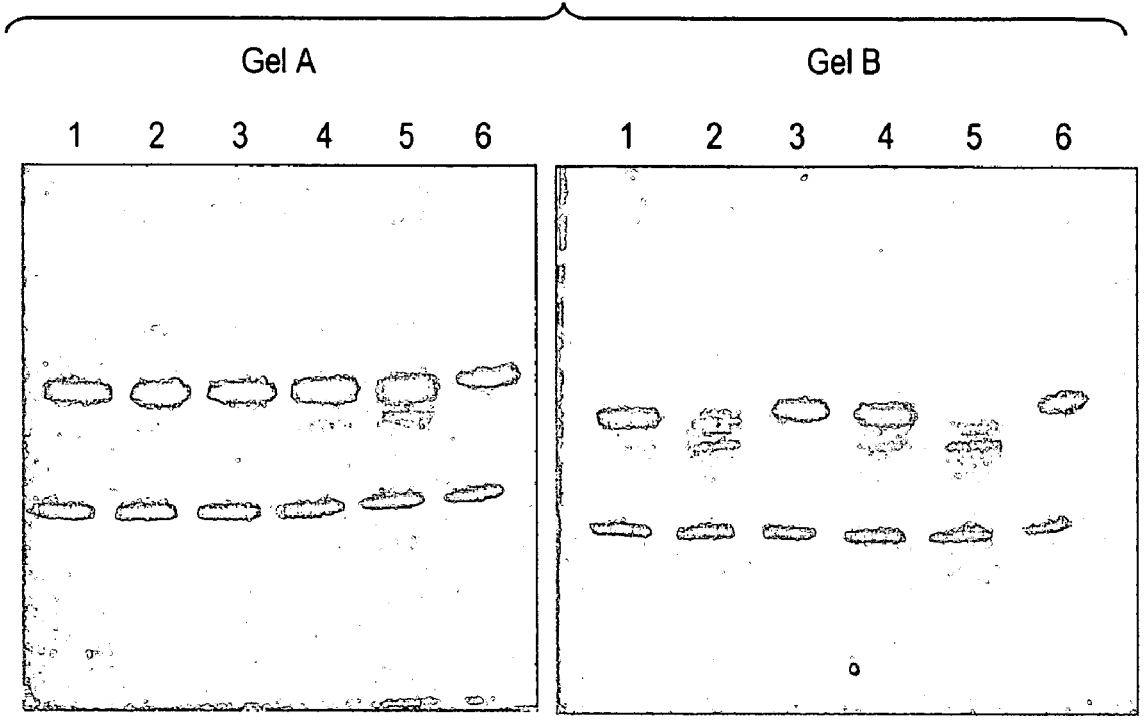

FIG. 17 shows the results of example 9 below. In this Figure, the alkaline-stabilized protein-based ligand and the MABSELECT™ ligand in red (lower level in both slides (red in original)) and green (upper bands in all lanes), respectively. In Gel A lanes 1-3 samples taken directly after mixing and 4-6 samples taken after 15 minutes incubation. In gel B lanes 1-3, 30 minutes and lanes 4-6, 60 minutes incubation. Lanes 1 and 4, 1 μg/mL and lanes 2 and 5, 5 μg/mL chymotrypsin in lanes 3 and 6 no enzyme added and serves as controls.

As appears from the figure, already after 15 minutes incubation a degradation of MABSELECT™ ligand can be seen while the alkaline-stabilized protein-based ligand stays intact when incubated with 5 μg/mL. After 30 minutes degradation becomes obvious for the 1 μg/mL chymotrypsin treated MABSELECT™ ligand. When incubated 60 minutes with 5 μg/mL no intact MABSELECT™ ligand can be detected. For the alkaline-stabilized protein-based ligand, no degradation can be observed for any of the tested conditions. In conclusion, the alkaline-stabilized protein-based ligand stays intact for one hour at 37° C. treated with 5 μg/mL chymotrypsin, whereas MABSELECT™ starts to degrade already after 15 minutes and becomes completely degraded after 60 minutes at the same conditions.

Figure 18:

FIG. 18 shows the results of example 9 below. In this Figure, the MABSELECT™ ligand (upper bands in all lanes (green in original)) and the alkaline-stabilized protein-based ligand (lower bands in all lanes (red in original)) incubated for 18 hours with (lane 2) or without (lane 3) CHO cell lysate at pH 5. Lane 1 is the sample before the incubation. As appears from FIG. 18, an obvious degradation of the MABSELECT™ ligand when incubated in CHO cell lysate at pH 5 for 18 hours at 37° C. can be seen. The alkaline-stabilized protein-based ligand stays intact when incubated with the same conditions. In conclusion, the alkaline-stabilized protein-based ligand is more protease stable than the MABSELECT™ ligand even in a CHO cell lysate.

DEFINITIONS

The term "protein" is used herein to describe proteins as well as fragments thereof. Thus, any chain of amino acids that exhibits a three dimensional structure is included in the term "protein", and protein fragments are accordingly embraced.

The term "functional variant" of a protein means herein a variant protein, wherein the function, in relation to the invention defined as affinity and stability, are essentially retained. Thus, one or more amino acids that are not relevant for said function may have been exchanged.

The term "parental molecule" is used herein for the corresponding protein in the form before a mutation according to the invention has been introduced.

The term "structural stability" refers to the integrity of three-dimensional form of a molecule, while "chemical stability" refers to the ability to withstand chemical degradation.

The term "Fc fragment-binding" protein means that the protein is capable of binding to the Fc fragment of an immunoglobulin. However, it is not excluded that an Fc fragment-binding protein also can bind other regions, such as Fab regions of immunoglobulins.

In the present specification, if not referred to by their full names, amino acids are denoted with the conventional one-letter symbols.

Mutations are defined herein by the number of the position exchanged, preceded by the wild type or non-mutated amino acid and followed by the mutated amino acid. Thus, for example, the mutation of an asparagine in position 23 to a threonine is denoted N23T.

The terms "immunoglobulin" and "antibody" will be used interchangeably herein.

The term "alkali-stable" refers to the improved alkaline stability obtained by the mutations according to the present invention.

DETAILED DESCRIPTION OF THE INVENTION

As appears from the above, one aspect of the invention is to reduce ligand leakage from protein-based ligands in a process for antibody purification. As is well known, leaked ligand frequently appears in the eluate as an antibody is released from protein-based affinity matrices. According to the present invention, ligand leakage may be reduced by reducing or substantially eliminating the binding of enzymes to the ligands, which will result in shorter contact time between ligand and enzyme and consequently a reduced leakage of ligand. The present inventors have unexpectedly found that an alkali-stable protein A-based ligand, wherein at least one asparagine residue has been mutated to an amino acid other than glutamine, is more stable to protease degradation than the conventionally used Protein A ligands.

Thus, in one embodiment, the present invention relates to a method of separating antibodies from protease, which method comprises
(a) contacting a liquid comprising antibodies and protease(s) with a separation matrix to adsorb antibodies;
(b) separating the liquid comprising protease(s) from the matrix; and, optionally,
(c) releasing the antibodies from the matrix by adding an eluent, the improvement being to use a separation matrix which comprises alkali-stable protein A-based ligands. In the most advantageous embodiment, the alkaline stability has been obtained by mutating at least one asparagine residue of an immunoglobulin-binding protein to an amino acid other than glutamine. In the present context, the term "alkali-stabilized" will be used for alkali-stable ligands which comprise one or more such mutations. In an advantageous embodiment, the antibodies are monoclonal antibodies.

Thus, an advantage of the invention is that by using the present method as a first chromatography step in an antibody process, the subsequent steps may be designed to capture other contaminants than ligand leakage, such as host cell proteins. Consequently, the present invention may enable antibody purification processes comprising fewer steps than the prior art.

In one embodiment, the ligands comprise at least one B domain of Protein A in which at least one asparagine residue has been mutated to an amino acid other than glutamine. In a specific embodiment, the ligands comprise at least one Protein Z domain in which at least one asparagine residue has been mutated to an amino acid other than glutamine. In a more specific embodiment, the protein ligands are multimers comprising two or more mutated Protein Z domains, wherein in each domain at least one asparagine residue has been mutated to an amino acid other than glutamine. The separation matrix used in the present method may use a separation matrix comprising anyone of the below-described ligands obtained by mutations of B domains and/or Protein Z domains. Thus, the separation matrix used in this method may comprise ligands which are multimers of the same or different alkali-stable protein A-based domains.

In an advantageous embodiment, the separation matrix is MABSURE™ or a functional equivalent thereof. In this context, a functional equivalent means any modified separation matrix, which retains the characteristics of binding antibodies while binding substantially no protease. As will be understood by the skilled person in this field, any protein which in its non-mutated form presents the amino acid sequence obtained by the herein described alkali-stability improving mutation(s) is also embraced by the present invention.

In another embodiment, the present invention is a method of reducing ligand leakage in a process for purifying antibodies, which method comprises
(a) contacting a liquid comprising antibodies and protease(s) with a separation matrix to adsorb antibodies;
(b) separating the liquid comprising protease(s) from the matrix; and, optionally,
(c) releasing the antibodies from the matrix by adding an eluent;

the improvement being to use a separation matrix which comprises alkali-stable protein A-based ligands wherein the alkaline stability has been obtained by mutating at least one asparagine residue of an immunoglobulin-binding protein to an amino acid other than glutamine. More specific embodiments of the alkali-stable protein A-based ligands may be as discussed above in the method of separating antibodies from proteases. In this context, the term "reduced" leakage is understood to be relative to the leakage obtained when using Protein A ligands which are not mutated under the equivalent conditions. In an advantageous embodiment, the antibodies are monoclonal antibodies.

In the most advantageous embodiment, the present method is a method of liquid chromatography.

In one aspect, the present invention relates to an immunoglobulin-binding protein capable of binding to other regions of the immunoglobulin molecule than the complementarity determining regions (CDR), wherein at least one asparagine residue of a parental immunoglobulin-binding protein has been mutated to an amino acid other than glutamine, which mutation confers an increased chemical stability at alkaline pH-values compared to the parental molecule. The increased stability means that the mutated protein's initial affinity for immunoglobulin is essentially retained for a prolonged period of time, as will be discussed below.

The retained affinity for the target protein achieved according to the invention is in part due to a retained spatial conformation of the mutant protein. The affinity of mutated proteins to immunoglobulins can for example be tested by the skilled person using biosensor technology using for example a BIA-CORE™ 2000 standard set-up (Biacore AB, Uppsala, Sweden), as will be illustrated in the experimental part below. In this context, it is understood from the term "essentially" retained that the mutated protein exhibits an affinity for immunoglobulin which is of the same order of magnitude as that of the parental molecule. Accordingly, in an initial phase, the binding capacity of the mutated protein is comparable with that of the parental molecule. However, due to the below-discussed chemical stability of the mutated protein, which is retained in time, its binding capacity will decrease more slowly than that of the parental molecule in an alkaline environment. The environment can be defined as alkaline, meaning of an increased pH-value, for example above about 10, such as up to about 13 or 14, i.e. from 10-13 or 10-14, in general denoted alkaline conditions. Alternatively, the conditions can be defined by the concentration of NaOH, which can be up to about 1.0 M, such as 0.7 M or specifically about 0.5 M, accordingly within a range of 7-1.0 M.

The increased chemical stability of the mutated protein according to the invention can easily be confirmed by the skilled person in this field e.g. by routine treatment with NaOH at a concentration of 0.5 M, as will be described in the experimental part below. In this context, it is to be understood that similar to what is said above, an "increased" stability means that the initial stability is retained during a longer period of time than what is achieved by the parental molecule. Even though similar mutations have been reported for a Streptococcal albumin-binding domain (Gülich et al, see above), it is well known that the rate of the deamidation involved in protein susceptibility to degradation in alkaline environments is highly sequence and conformation dependent. Since the amino acid sequence of ABD comprises no amino acid sequence similarity to immunoglobulin-binding proteins such as the individual domains staphylococcal protein A, it would not appear as though the teachings of Gülich et al could be applied also to immunoglobulin-binding proteins. However, the present invention shows for the first time that mutation of one or more asparagine residues of an immunoglobulin-binding protein surprisingly provides an improved chemical stability and hence a decreased degradation rate in environments wherein the pH is above about 10, such as up to about 13 or 14.

Thus, the present invention provides a mutated protein, which is useful e.g. as a protein ligand in affinity chromatography for selective adsorption of immunoglobulins, such as IgG, IgA and/or IgM, preferably IgG, from a mammalian species, such as a human. The purpose of the adsorption can be either to produce a purified product, such as a pure immunoglobulin fraction or a liquid from which the immunoglobulin has been removed, or to detect the presence of immunoglobulin in a sample. The ligand according to the invention exhibits a chemical stability sufficient to withstand conventional alkaline cleaning for a prolonged period of time, which renders the ligand an attractive candidate for cost-effective large-scale operation where regeneration of the columns is a necessity.

Accordingly, in the protein according to the invention, one or more asparagine (N) residues have been mutated to amino acids selected from the group that consists of glycine (G), alanine (A), valine (V), leucine (L), isoleucine (I), serine (S), threonine (T), cysteine (C), methionine (M), phenylalanine (F), tyrosine (Y), tryptophan (W), glutamic acid (E), arginine (R), histidine (H), lysine (K) or proline (P), or any modified amino acid that is not susceptible to the undesired deamidation and isomerisation. Alternatively, one or more asparagine (N) residues have been mutated to glutamine (Q).

The immunoglobulin-binding protein can be any protein with a native immunoglobulin-binding capability, such as Staphylococcal protein A (SpA) or Streptococcal protein G (SpG). For a review of other such proteins, see e.g. Kronvall, G., Jonsson, K. Receptins: a novel term for an expanding spectrum of natural and engineered microbial proteins with binding properties for mammalian proteins, *J. Mol. Recognit.* 1999 January-February; 12(1):38-44. Review.

In one embodiment, the present invention is a mutated protein, which comprises at least the binding region of an immunoglobulin-binding protein and wherein at least one such asparagine mutation is present within said region. Accordingly, in this embodiment, a mutated protein according to the invention comprises at least about 75%, such as at least about 80% or preferably at least about 95%, of the sequence as defined in SEQ ID NOs: 1 or 2, with the proviso that the asparagine mutation is not in position 21.

In the present specification, SEQ ID NO: 1 defines the amino acid sequence of the B-domain of SpA and SEQ ID NO: 2 defines a protein known as protein Z. Protein Z is synthetic construct derived from the B-domain of SpA, wherein the glycine in position 29 has been exchanged for alanine, and it has been disclosed in the literature, see e.g. Ståhl et al, 1999: Affinity fusions in biotechnology: focus on protein A and protein G, in The Encyclopedia of Bioprocess Technology: Fermentation, Biocatalysis and Bioseparation. M. C. Fleckinger and S. W. Drew, editors. John Wiley and Sons Inc., New York, 8-22. Further, protein Z has been used both as a ligand in affinity chromatography. However, even though protein Z exhibits an improved chemical stability to certain chemicals other than NaOH as compared to the SpA B-domain, it is still not as stable in conditions of increased pH-values as required to withstand the many CIP regeneration steps desired in an economic industrial plant.

In one embodiment, the above described mutant protein is comprised of the amino acid sequence defined in SEQ ID NOs: 1 or 2, or is a functional variant thereof. The term "functional variant" as used in this context includes any similar sequence, which comprises one or more further variations in amino acid positions that have no influence on the mutant protein's affinity to immunoglobulins or its improved chemical stability in environments of increased pH-values.

In an advantageous embodiment, the present mutation(s) are selected from the group that consists of N23T; N23T and N43E; N28A; N6A; N11S; N11S and N23T; and N6A and N23T; and wherein the parental molecule comprises the sequence defined by SEQ ID NO: 2. As mentioned above, in order to achieve a mutant protein useful as a ligand with high binding capacity for a prolonged period of time in alkaline conditions, mutation of the asparagine residue in position 21 is avoided. In one embodiment, the asparagine residue in position 3 is not mutated.

In the most advantageous embodiment, in the present protein, an asparagine residue located between a leucine residue and a glutamine residue has been mutated, for example to a threonine residue. Thus, in one embodiment, the asparagine residue in position 23 of the sequence defined in SEQ ID NO: 2 has been mutated, for example to a threonine residue. In a specific embodiment, the asparagine residue in position 43 of the sequence defined in SEQ ID NO: 2 has also been mutated, for example to a glutamic acid. In the embodiments where amino acid number 43 has been mutated, it appears to most advantageously be combined with at least one further mutation, such as N23T.

The finding according to the invention that the various asparagine residues of the B-domain of SpA and protein Z can be ascribed different contributions to affinity and stability properties of the mutated protein was quite unexpected, especially in view of the above discussed teachings of Gülich et al wherein it was concluded that all the asparagine residues of ABD could be mutated without any internal discrimination. Thus, the invention encompasses the above-discussed monomeric mutant proteins. However, such protein monomers can be combined into multimeric proteins, such as dimers, trimers, tetramers, pentamers etc. Accordingly, another aspect of the present invention is a multimer comprised of at least one of the mutated proteins according to the invention together with one or more further units, preferably also mutant proteins according to the invention. Thus, the present invention is e.g. a dimer comprised of two repetitive units.

In one embodiment, the multimer according to the invention comprises monomer units linked by a stretch of amino acids preferably ranging from 0 to 15 amino acids, such as 5-10. The nature of such a link should preferably not destabilise the spatial conformation of the protein units. Furthermore, said link should preferably also be sufficiently stable in alkaline environments not to impair the properties of the mutated protein units.

In the best embodiment at present, the multimer is a tetramer of protein Z comprising the mutation N23T, wherein the length of the linking units are 5-10 amino acids. In one embodiment, the present multimer comprises the sequence VDAKFN-Z(N23T)-QAPKVDAKFN-Z(N23T)QAPKC (SEQ ID NO: 22). In another embodiment, the multimer comprises the sequence VDAKFD-Z(N23T)-QAPKVDAKFD-Z(N23T)-ZQAPKC (SEQ ID NO: 23).

In a specific embodiment, the present multimer also comprises one or more of the E, D, A, B, and C domains of Staphylococcal protein A. In this embodiment, it is preferred that asparagine residues located in loop regions have been mutated to more hydrolysis-stable amino acids. In an embodiment advantageous for structural stability reasons, the glycine residue in position 29 of SEQ ID NO: 1 has also been mutated, preferably to an alanine residue. Also, it is advantageous for the structural stability to avoid mutation of the asparagine residue in position 52, since it has been found to contribute to the α-helical secondary structure content of the protein A molecule.

In a further aspect, the present invention relates to a nucleic acid encoding a mutant protein or multimer as described above. Accordingly, the invention embraces a DNA sequence that can be used in the production of mutant protein by expression thereof in a recombinant host according to well-established biotechnological methods. Consequently, another aspect of the present invention is an expression system, which enables production of a mutant protein as described above. Bacterial hosts can conveniently be used, e.g. as described in the experimental part below. In an alternative embodiment, the present invention is a cell line that has been genetically manipulated to express a mutant protein according to the invention. For methods to this end, see e.g. Sambrook et al., Molecular Cloning: A Laboratory Manual ($2^{nd}$ ed), vols. 1-3, Cold Spring Harbor Laboratory, (1989).

Naturally, once the desired sequence has been established, the mutant protein according to the invention can alternatively be produced by synthetic methods.

Accordingly, the present invention also includes a biotechnological or synthetic method of producing a mutant protein or a multimer according to the invention.

In another aspect, the present invention relates to a matrix for affinity separation, which matrix comprises ligands that comprise immunoglobulin-binding protein coupled to a solid support, in which protein at least one asparagine residue has been mutated to an amino acid other than glutamine. The present matrix, when compared to a matrix comprised of the parental molecule as ligand, exhibits an increased binding capacity during two or more separations with intermittent alkaline cleaning. The mutated protein ligand is preferably an Fc-fragment-binding protein, and can be used for selective binding of IgG, IgA and/or IgM, preferably IgG.

The matrix according to the invention can comprise the mutant protein as described above in any embodiment thereof as ligand. In the most preferred embodiment, the ligands present on the solid support comprise a multimer as described above.

The solid support of the matrix according to the invention can be of any suitable well-known kind A conventional affinity separation matrix is often of organic nature and based on polymers that expose a hydrophilic surface to the aqueous media used, i.e. expose hydroxy (—OH), carboxy (—COOH), carboxamido (—CONH$_2$, possibly in N-substituted forms), amino (—NH$_2$, possibly in substituted form), oligo- or polyethylenoxy groups on their external and, if present, also on internal surfaces. In one embodiment, the polymers may, for instance, be based on polysaccharides, such as dextran, starch, cellulose, pullulan, agarose etc, which advantageously have been cross-linked, for instance with bisepoxides, epihalohydrins, 1,2,3-trihalo substituted lower hydrocarbons, to provide a suitable porosity and rigidity. In the most preferred embodiment, the solid support is porous agarose beads. The supports used in the present invention can easily be prepared according to standard methods, such as inverse suspension gelation (S Hjertén: Biochim Biophys Acta 79(2), 393-398 (1964). Alternatively, the base matrices are commercially available products, such as SEPHAROSE™ FF (Amersham Biosciences, Uppsala, Sweden). In an embodiment, which is especially advantageous for large-scale separations, the support has been adapted to increase its rigidity, and hence renders the matrix more suitable for high flow rates.

Alternatively, the solid support is based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (Amersham Biosciences, Uppsala, Sweden) is used.

In another alternative, the solid support according to the invention comprises a support of inorganic nature, e.g. silica, zirconium oxide etc.

In yet another embodiment, the solid support is in another form such as a surface, a chip, capillaries, or a filter.

As regards the shape of the matrix according to the invention, in one embodiment the matrix is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batch-wise mode will be used.

The ligand may be attached to the support via conventional coupling techniques utilising, e.g. amino and/or carboxy groups present in the ligand. Bisepoxides, epichlorohydrin, CNBr, N-hydroxysuccinimide (NHS) etc are well-known coupling reagents. Between the support and the ligand, a molecule known as a spacer can be introduced, which will improve the availability of the ligand and facilitate the chemical coupling of the ligand to the support. Alternatively, the ligand may be attached to the support by non-covalent bonding, such as physical adsorption or biospecific adsorption.

In an advantageous embodiment, the present ligand has been coupled to the support by thioether bonds. Methods for performing such coupling are well-known in this field and easily performed by the skilled person in this field using standard techniques and equipment. In an advantageous embodiment, the ligand is firstly provided with a terminal cysteine residue for subsequent use in the coupling. The skilled person in this field also easily performs appropriate steps of purification.

As mentioned above, the affinity to immunoglobulin i.e. the binding properties of the present ligand, and hence the capacity of the matrix, is not essentially changed in time by treatment with an alkaline agent. Conventionally, for a cleaning in place treatment of an affinity separation matrix, the alkaline agent used is NaOH and the concentration thereof is up to 0.75 M, such as 0.5 M.

Thus, another way of characterising the matrix according to the invention is that due to the above discussed mutations, its binding capacity will decrease to less than about 70%, preferably less than about 50% and more preferably less than about 30%, such as about 28%, after treatment with 0.5 M NaOH for 7.5 h.

In a further aspect, the present invention relates to a method of isolating an immunoglobulin, such as IgG, IgA and/or IgM, wherein a mutant protein, a multimer or a matrix according to the invention is used. Thus, the invention encompasses a process of chromatography, wherein at least one target compound is separated from a liquid by adsorption to a mutant protein or a multimer or matrix described above. The desired product can be the separated compound or the liquid. Thus, this aspect of the invention relates to affinity chromatography, which is a widely used and well-known separation technique. In brief, in a first step, a solution comprising the target compounds, preferably antibodies as mentioned above, is passed over a separation matrix under conditions allowing adsorption of the target compound to ligands present on said matrix. Such conditions are controlled e.g. by pH and/or salt concentration i.e. ionic strength in the solution. Care should be taken not to exceed the capacity of the matrix, i.e. the flow should be sufficiently slow to allow a satisfactory adsorption. In this step, other components of the solution will pass through in principle unimpeded. Optionally, the matrix is then washed, e.g. with an aqueous solution, in order to remove retained and/or loosely bound substances. The present matrix is most advantageously used with a washing step utilising an alkaline agent, as discussed above. In a next step, a second solution denoted an eluent is passed over the matrix under conditions that provide desorption i.e. release of the target compound. Such conditions are commonly provided by a change of the pH, the salt concentration i.e. ionic strength, hydrophobicity etc. Various elution schemes are known, such as gradient elution and step-wise elution. Elution can also be provided by a second solution comprising a competitive substance, which will replace the desired antibody on the matrix. For a general review of the principles of affinity chromatography, see e.g. Wilchek, M., and Chaiken, I. 2000. An overview of affinity chromatography. *Methods Mol. Biol.* 147: 1-6.

In an alternative embodiment, a mutant protein according to the invention is used as a lead compound in a process wherein an organic compound is modelled to resemble its three dimensional structure. The so modelled compound is known as a mimetic.

Mimetic design, synthesis and testing can be used to avoid randomly screening large number of molecules. In brief, such a method can involve determining the particular parts of the protein that are critical and/or important for a property such as immunoglobulin-binding. Once these parts have been identified, its structure is modelled according to its physical properties, e.g. stereochemistry, bonding, size, charge etc using data from a range of sources, such as spectroscopic techniques, X-ray diffraction data and NMR. Computational analysis, similarity mapping and other techniques can be used in this process. Important considerations in this kind of process are the ease to synthesise a compound, pharmacological acceptance, degradation pattern in vivo etc.

Finally, the present invention also comprises other uses of the mutant protein described above, such as in analytical methods, for medical purposes, e.g. for diagnosis, in arrays etc.

EXAMPLES

Below, the present invention will be described by way of examples, which are provided for illustrative purposes only and accordingly are not to be construed as limiting the scope of the present invention as defined by the appended claims. All references given below and elsewhere in this application are hereby included herein by reference.

In this part, since Z in its original form already has a significant but non-sufficient stability towards alkaline treatment, it was assumed that small changes in stability due to the mutations would be difficult to assess in laboratory testings. Therefore, a suppressor mutation method (Kotsuka, T., S. Akanuma, M. Tomuro, A. Yamagishi, and T. Oshima. 1996. Further stabilisation of 3-isopropylmalate dehydrogenase of an extreme thermophile, *Thermus thermophilus*, by a suppressor mutation method. *J. Bacteriol.* 178:723-727; and Sieber, V., A. Plückthun, and F. X. Schmidt. 1998. Selecting proteins with improved stability by a phage-based method. *Nature Biotechnology.* 16:955-960) was used to provide a variant of the Z domain with a decreased structural stability. According to this strategy the destabilised variant of protein Z, herein denoted Z(F30A) (Cedergren et al., 1993, supra) was used as scaffold for subsequent introduction of additional mutations related to investigations of alkaline stability. The binding properties of this variant are similar to native protein Z, since F30 is not involved in the Fc-binding.

Further, Zwt denotes the wild type Z domain, not containing the F30A substitution.

Experimental Strategy

Figure 1:
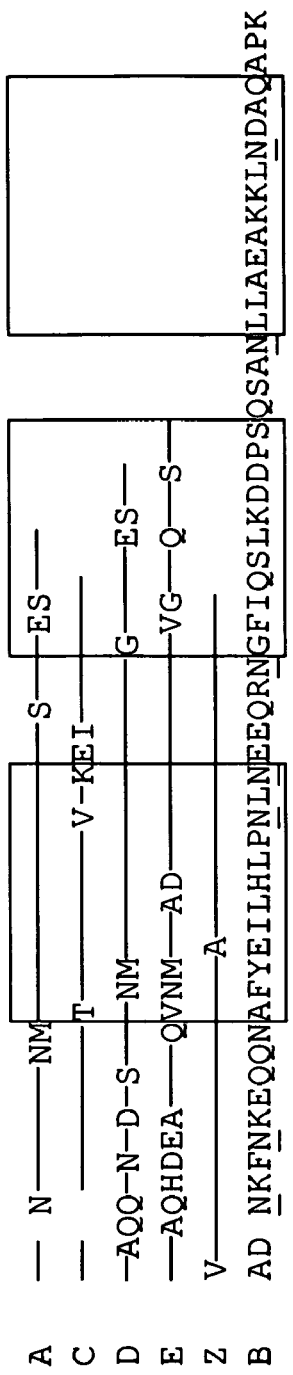

To analyze which asparagines in the Z domain that are responsible for its instability in alkaline conditions, a mutational analysis was performed. In order to enable detection of improvements regarding the alkaline stability of the Z domain, it was decided to use a mutated variant, Z(F30A), since the Z-domain already possesses a significant but non-sufficient stability towards alkaline conditions. Z(F30A) has earlier been shown to possess an affinity to IgG that is similar to the wild type, but also a remarkably decreased structural stability due to the mutation of an amino acid that normally takes part in the hydrophobic core (Cedergren et al., 1993, supra; Jendeberg, L., B. Persson, R. Andersson, R. Karlsson, M. Uhlen, and B. Nilsson. 1995. Kinetic analysis of the interaction between protein A domain variants and human Fc using plasmon resonance detection. *Journal of Molecular Recognition.* 8:270-278). The Z-domain is a three-helix bundle consisting of 58 amino acids, including eight asparagines (N3, N6, N11, N21, N23, N28, N43 and N52) (FIG. 1) (Nilsson, B., T. Moks, B. Jansson, L. Abrahmsen, A. Elmblad, E. Holmgren, C. Henrichson, T. A. Jones, and M. Uhlen. 1987. A synthetic IgG-binding domain based on staphylococcal protein A. *Protein Eng.* 1:107-113). To evaluate the effect of the different asparagines on the deactivation rate in alkaline conditions, seven of these residues were exchanged for other amino acids. Since N3 is located in the flexible amino-terminal of the domain, it was excluded from the study. It was assumed that a degradation of this amino acid would not affect the activity of a monomeric ligand and would therefore not be detectable in the present assay, which measures the retained activity. Moreover, since the amino acid is located outside the structured part of the domain it will presumably be easily replaceable during a multimerisation of the domain to achieve a protein A-like molecule. To facilitate the protein design, a comparison with the homologous sequences from the other domains of protein A was made (FIG. 1). From the comparison, it was decided to exchange asparagine 11 for a serine and 23 for threonine and finally 43 for a glutamic acid. Asparagine 6 was exchanged for alanine since the alternative when looking on the homologous sequences was aspartic acid, which also has been reported to be sensitive in alkaline conditions. All five domains of protein A have asparagines in the other positions (21, 28, 52). Hence, they were exchanged for alanines.

Example 1

Mutagenesis, Expression and Purification of Mutant Protein Z

Materials and Methods

Site-directed mutagenesis was performed using a two-step PCR-technique (Higuchi et al., 1988). Plasmid pDHZF30A (Cedergren et al., 1993) was used as template. Oligonucleotides coding for the different asparagine replacements and the A29G replacement were synthesised by Interactiva (Interactiva Biotechnologie GmbH, Ulm, Germany). The restriction enzymes XbaI and HindIII (MBI Fermentas Inc., Amhurst, N.Y.) were used for cloning into the vector pDHZ (Jansson et al., 1996) that was performed according to Sambrook (Sambrook et al., 1987). To create pTrpZ, the Z domain was amplified by PCR, using plasmid pKN1 as template (Nord et al., 1995). The fragment was restricted with XbaI and PstI and ligated into the vector pTrpABDT1T2 (Kraulis et al., 1996) that had been restricted with same enzymes. A MEGABACE™ 1000 DNA Sequencing System (Amersham Biosciences, Uppsala, Sweden) was used to verify correct sequence of inserted fragments. MEGABACE™ terminator chemistry (Amersham Biosciences, Uppsala, Sweden) was utilised according to the supplier's recommendations in a cycle sequencing protocol based on the dideoxy method (Sanger et al., 1977). During cloning procedures, *Escherichia coli* strain RR1ΔM15 (American Type Culture Collection, Rockville, Mass.) was used, whereas for expression of the different gene products 017 (Olsson, M. O., and L. A. Isaksson. 1979. Analysis of rpsD Mutations in *Escherichia coli*. I: Comparison of Mutants with Various Alterations in Ribosomal Protein S4. *Molec. gen. Genet.* 169:251-257) was used.

Production and purification of Z(F30A) and the different constructs thereof were performed according to the protocol outlined by Gülich (Gülich et al., 2000b, see above). The production of Z and pZ(N23T) were performed as described in Kraulis et al (Kraulis, P. J., P. Jonasson, P.-Å. Nygren, M. Uhlén, L. Jendeberg, B. Nilsson, and J. Kordel. 1996. The serum albumin-binding domain of streptococcal proteinG is a three-helix bundel: a heteronuclear NMR study. *FEBS lett.* 378:190-194). Relevant fractions were lyophilised. The amount of protein was estimated by absorbance measurements at 280 nm using the specific absorbance coefficient, a (1 g$^{-1}$ cm$^{-1}$), Z 0.156; Z(N23T), 0.169; Z(F30A), Z(F30A, N43E), Z(F30A,N23T,N43E) 0.157; Z(F30A,N6A), Z(F30A,N11S), Z(F30A,N21A), Z(F30A,N23T), Z(F30A, N28A), Z(F30A,N52A), Z(F30A,N6A,N23T), Z(F30A, N11S,N23T) 0.158. The concentration was confirmed by amino acid analysis (BMC, Uppsala, Sweden). The homogeneity was analysed by Sodium Dodecyl Sulfate PolyAcrylamide Gel Electrophoresis (SDS-PAGE) (Laemmli, U. K. 1970. Cleavage of Structural Proteins during the Assembly of the Head of Bacteriophage T4. *Nature.* 227:680-685) using the PHAST™ system (Amersham Biosciences, Uppsala, Sweden). Lyophilised proteins were loaded on high-density gels (Amersham Biosciences, Uppsala, Sweden) under reducing conditions and stained with Coomassie Brilliant Blue according to the supplier's recommendations. The homogeneity and the molecular weights were further confirmed by mass spectrometry.

For CD spectroscopy, protein samples were prepared in a phosphate buffer (8.1 mM K$_2$HPO$_4$, 1.9 mM KH$_2$PO$_4$, pH 7.5) to a concentration of 10 μM. Spectra were recorded using a J-720 spectropolarimeter (JASCO, Tokyo, Japan) in the far UV region from 250 to 200 nm at RT in a quartz cell of path length 0.1 cm and with a scan speed of 10 nm min$^{-1}$. Each spectrum was the mean of five accumulated scans and the final spectra were converted into mean residue ellipticity (MRE) (deg cm$^2$ dmol$^{-1}$).

Results (Example 1)

All Z variants were successfully produced intracellular in E. coli at 37° C. and show the same expression levels, approximately 50 mg/l as estimated from SDS-PAGE. The proteins were all purified by IgG affinity chromatography. After the purification, samples were analysed with SDS-PAGE (data not shown), lyophilised and stored for further analyses. The molecular mass for protein Z and the different mutants thereof were also confirmed by mass spectrometry. The data confirmed correct amino acid content for all mutants (data not shown). Also, structural analyses were performed on a Circular Dichroism (CD) equipment, since it previously has been proven to be suitable for detecting structural changes in α-helical proteins (Johnson, C. W., Jr. 1990. Protein secondary structure and circular dichroism: a practical guide. *Proteins.* 7:205-214; and Nord, K., J. Nilsson, B. Nilsson, M. Uhlén, and P.-Å. Nygren. 1995. A combinatorial library of an α-helical bacterial receptor domain. *Prot. eng.* 8:601-608). All spectra show a minimum at 208 nm and at 222 nm in combination with a maximum around 195 nm, indicating a similar structure for the mutants and the parental molecule. However, Z(F30A,N52A) seems to have a somewhat lower α-helicity than the wild type Z and the other mutants thereof (data not shown).

Example 2

Biospecific Interaction Analysis

Materials and Methods

Differences in affinity and kinetic constants of the association and dissociation states were detected on a BIACORE™ 2000 instrument (Biacore, Uppsala, Sweden). Human polyclonal IgG and HSA (negative reference) were immobilised by amine coupling on the carboxylated dextran layer of a CM5 sensor chip (Biacore) according to the supplier's recommendations. The immobilisation of IgG resulted in approximately 2000 RU. Z, ZF30A, and the different mutants were prepared in HBS (10 mM HEPES, 0.15 M NaCl, 3.4 mM EDTA, 0.005% surfactant P20, pH 7.4) at 10 different concentrations (100-550 nM). The samples were injected over the surfaces as duplicates in random order at a flow rate of 30 μl min$^{-1}$. 10 mM HCl was used to regenerate the surface. The data was analysed using the BIA evaluation 3.0.2b software (Biacore AB). The signals from a control surface immobilized with HSA were subtracted from the IgG surface. A 1:1 Langmuir model was assumed and apparent kinetic constants and also affinity constants were calculated. Also, the change in free binding energy ($\Delta\Delta G = -RT \ln K_{aff, mutant}/K_{aff, native}$) in relation to the native molecule was calculated.

Results (Example 2)

To determine the differences in affinity for the Z variants towards IgG, surface plasmon resonance (SPR) using a BIACORE™ 2000 instrument was carried out. The aim was to compare the affinity for the different mutated Z variants according to the invention with the parental molecule. As mentioned above, due to the high alkaline stability of the parental Z domain it was decided to use a structurally destabilised variant of Z including the F30A mutation (Cedergren, L., R. Andersson, B. Jansson, M. Uhlén, and B. Nilsson. 1993. Mutational analysis of the interaction between staphylococcal protein A and human IgG$_1$. *Protein eng.* 6:441-448). Therefore, it was of importance to first confirm that the affinity between the mutated molecule and IgG was retained despite the mutation. As can be seen in table 1 below, the affinity of Z(F30A) is not significantly affected. The very small change in affinity gives a slightly higher stability to the complex of Z(F30A) and IgG compared to the parental molecule Z and IgG. This is in accordance with results earlier reported by Jendeberg et al. (Cedergren et al., 1993, supra; Jendeberg et al., 1995, supra). All mutants constructed with Z(F30A) as scaffold were analysed and compared with their parental molecule (Z(F30A)). The results show that the overall affinity is not significantly affected by the mutations, indicating that none of the asparagine mutations according to the invention are very important for the binding to IgG (see table 1 below). In all Z variants including the N21A or the N43E mutation, only a slightly lower affinity constant was observed. For mutants with the N23T mutation, surprisingly, the affinity even seems to be slightly higher. Also, in the case of the N28A-mutation, the decrease in affinity is very small, and cannot be expected to have any essential influence if the mutant protein is used e.g. as a protein ligand. Furthermore, all constructs including the N28A-mutation have a remarkably increased off-rate. For the mutants including the N23T mutation the somewhat increased affinity seems to be due to a slightly increased on-rate. Also, the N6A-mutation gives a higher on-rate, but the affinity constant is not affected because of the increased off-rate that also follows the mutation.

TABLE 1

An overview of the kinetic study on the different Z domains carried out using the BIACORE ™ 2000 instrument.

| Mutant | kon [$10^5$ M$^{-1}$ s$^{-1}$] | koff [$10^{-3}$ s$^{-1}$] | Kaff [$1 10^7$ M$^{-1}$] | ΔΔG (vs Zwt) [kcal/mol] | ΔΔG (vs Z(F30A)) [kcal/mol] |
|---|---|---|---|---|---|
| Zwt | 1.5 | 3.7 | 4.0 | 0 | |
| Z(N23T) | 2.7 | 3.9 | 7 | −0.3 | |
| Z(F30A) | 1.9 | 4.17 | 4.5 | −0.1 | 0.0 |
| Z(F30A, N6A) | 7 | 21 | 3.3 | 0.1 | 0.2 |
| Z(F30A, N11S) | 1.6 | 4.9 | 3.2 | 0.1 | 0.2 |
| Z(F30A, N21A) | 1 | 3.8 | 2.6 | 0.3 | 0.4 |
| Z(F30A, N23T) | 2.1 | 3.75 | 5.6 | −0.2 | −0.1 |
| Z(F30A, N28A) | 3.1 | 9.87 | 3.2 | 0.1 | 0.2 |

TABLE 1-continued

An overview of the kinetic study on the different Z domains carried out using the BIACORE ™ 2000 instrument.

| Mutant | kon $[10^5 M^{-1} s^{-1}]$ | koff $[10^{-3} s^{-1}]$ | Kaff $[1 10^7 M^{-1}]$ | ΔΔG (vs Zwt) [kcal/mol] | ΔΔG (vs Z(F30A)) [kcal/mol] |
|---|---|---|---|---|---|
| Z(F30A, N43E) | 1.3 | 5.1 | 2.6 | 0.3 | 0.4 |
| Z(F30A, N52A) | 1.5 | 4.9 | 3 | 0.2 | 0.3 |
| Z(F30A, N23T, N43E) | 0.8 | 3.8 | 2 | 0.4 | 0.5 |

Zwt was used as an internal standard during the different measurements. The differences in free binding energy are calculated relative to Zwt and Z(F30A) respectively.

Example 3

Stability Towards Alkaline Conditions

Materials and Methods

The behaviour of the variants of domain Z as affinity ligands was analysed by immobilisation to a standard affinity matrix. Z, Z(F30A), and mutated variants were covalently coupled to HITRAP™ affinity columns (Amersham Biosciences, Uppsala, Sweden) using the N-hydroxysuccinimide chemistry according to the manufacturer's recommendations. The columns were pulsed with TST and 0.2 M HAc, pH 3.1. Human polyclonal IgG in TST was prepared and injected onto the columns in excess. A standard affinity chromatography protocol was followed for 16 cycles on the ÄKTA™ explorer 10 (Amersham Biosciences, Uppsala, Sweden). Between each cycle a CIP-step was integrated. The cleaning agent was 0.5 M NaOH and the contact time for each pulse was 30 minutes, resulting in a total exposure time of 7.5 hours. Eluted material was detected at 280 nm.

Results (Example 3)

Figure 2A:
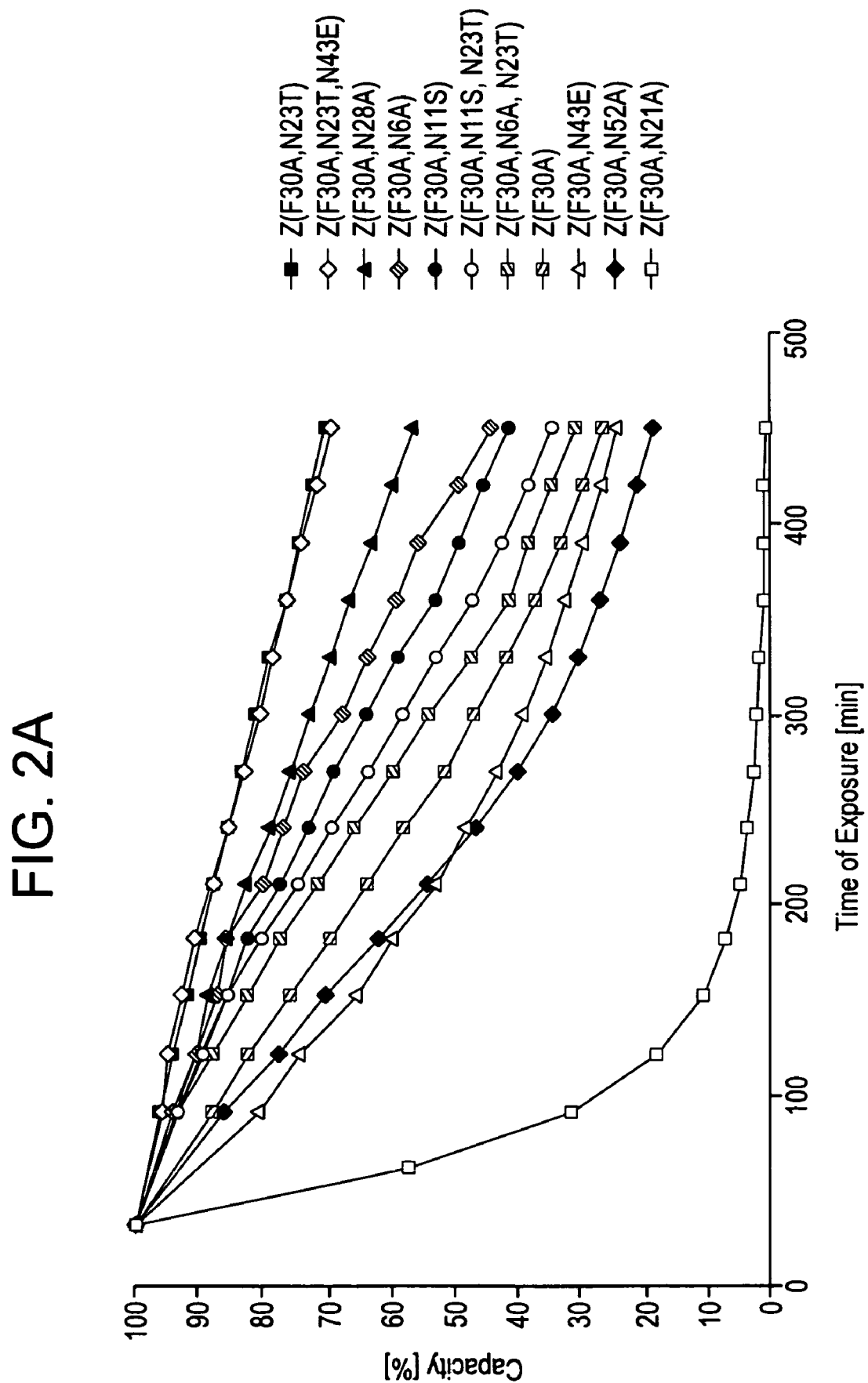

Z, Z(F30A), and mutants thereof were covalently attached to HITRAP™ columns using NHS-chemistry. IgG in excess was loaded and the amount of eluted IgG was measured after each cycle to determine the total capacity of the column. Between each cycle the columns were exposed to CIP treatment consisting of 0.5 M NaOH. After 16 pulses, giving a total exposure time of 7.5 hours, the column with the Z(F30A)-matrix shows a 70% decrease of the capacity. The degradation data in FIG. 2a suggest that four of the exchanged asparagines (N6, N11, N43 and N52) are less sensitive to the alkaline conditions the mutants are exposed for in this experiment. In contrast, N23 seems to be very important for the stability of Z(F30A). Z(F30A,N23T) shows only a 28% decrease of capacity despite the destabilising F30A-mutation. Hence, the Z(F30A,N23T) is almost as stable as Zwt and thereby the most stabilised variant with Z(F30A) as scaffold. Also the Z(F30A)-domain with two additional mutations Z(F30A,N23T,N43E) shows the same pattern of degradation as Z(F30A,N23T). An exchange of N28 to an alanine also improves the stability of Z(F30A) towards alkaline conditions. Surprisingly, the column with Z(F30A,N21A) as affinity ligand reveals a dramatic loss of capacity when exposed to NaOH compared to the parental molecule. These data make Z(N23T) to a very advantageous candidate as ligand in affinity purification of IgG.

Figure 2B:
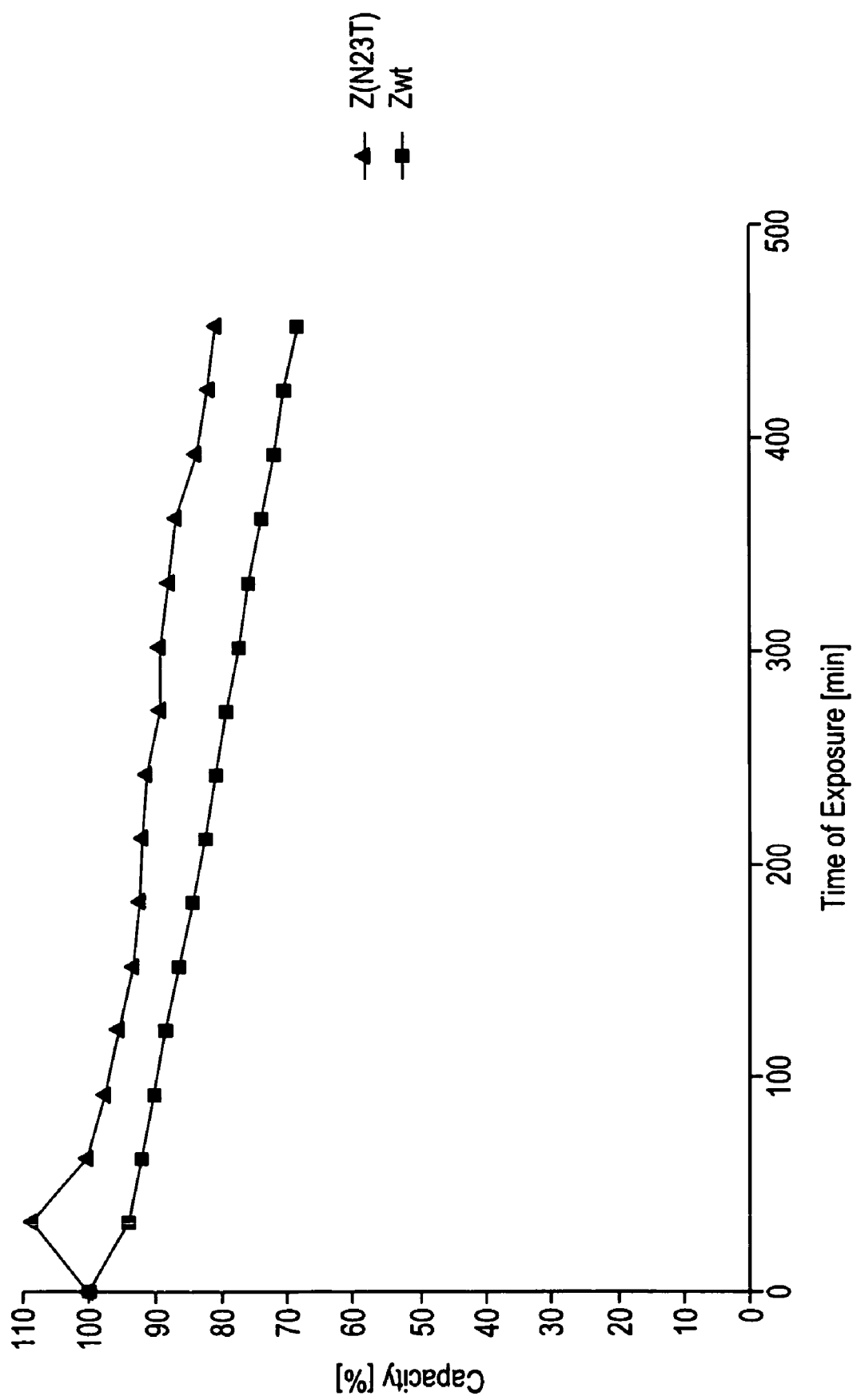
Figure 4:
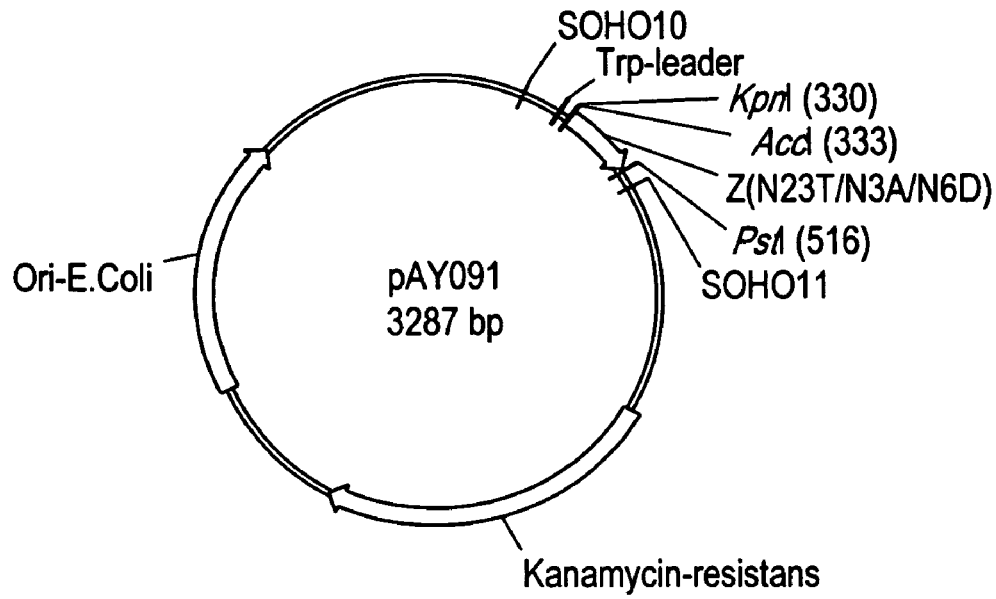
FIG. 4 shows a plasmid map of the plasmid pAY91, which contains the gene encoding Z(N23T/N3A/N6D)-Cys as described in example 4(a).
Figure 6:
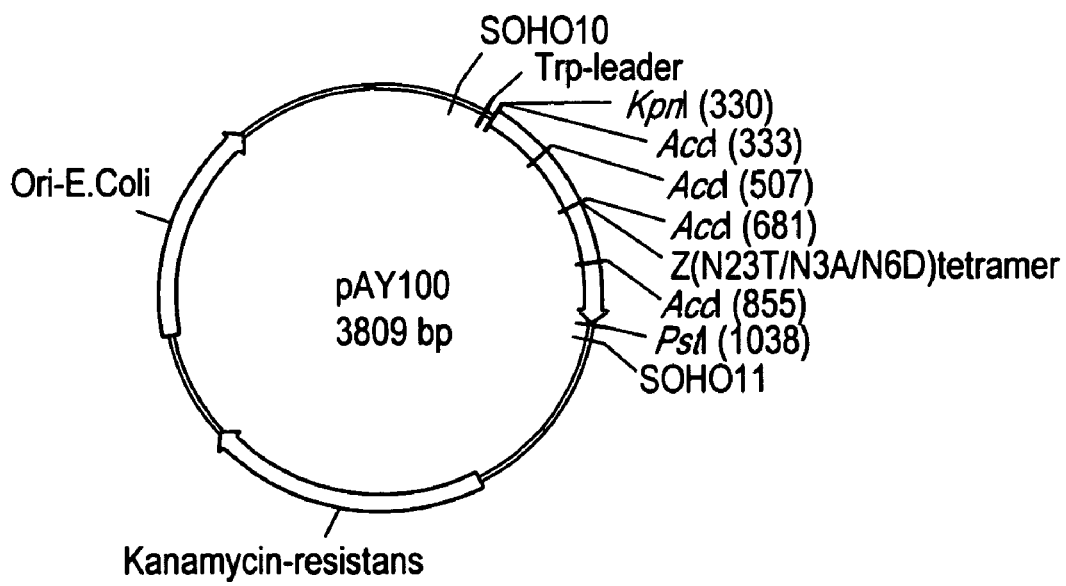
FIG. 6 shows an example of plasmid map for the plasmid pAY100 expressing the tetramer of Z(N23T/N3A/N6D)-Cys as described in example 5.

To finally prove the reliability of the strategy using a structurally destabilised variant of a molecule in order to make small changes in stability detectable, the N23T-mutation was grafted into the parental Z-domain. Both the parental Z-domain and Z(N23T) were coupled to HITRAP™-columns and exposed to alkaline conditions in the same way as for the already mentioned mutants. As can be seen in FIG. 2b, the Z(N23T)-mutant shows higher stability than Zwt when exposed to high pH.

Example 4

Construction of Monomers of Z-Mutants with and without a C-Terminal Cysteine Three different mutations were introduced in a gene encoding Z(N23T): K4G, N3A and the double-mutation N3A/N6D.

The mutations were originally introduced into two different vectors: one with a cysteine in the C-terminus and one without the cysteine. This was done to later facilitate the construction of multimers with one single C-terminal cysteine.

Example 4(a)

Cysteine-Containing Monomer Construction

As template for the construction, a plasmid denoted "pGEM ZN23T", was used. This already contained the N23T-mutation in the Z-gene.

A PCR-reaction was performed with this plasmid as template and the two oligonucleotides

```
AFFI-63: TTT TTT GTA GAC AAC GGA TTC AAC AAA GAA C

GRTO-40: GAT CTG CTG CAG TTA GCA TTT CGG CGC CTG
         AGC ATC ATT TAG
``` for the K4G-mutation (SEQ ID NOs: 24-25),

```
AFFI-64: TTT TTT GTA GAC GCC AAA TTC AAC AAA GAA C

GRTO-40: GAT CTG CTG CAG TTA GCA TTT CGG CGC CTG
         AGC ATC ATT TAG
``` for the N3A-mutation and (SEQ ID NOs: 26-27),

```
AFFI-65: TTT TTT GTA GAC GCC AAA TTC GAC AAA GAA C

GRTO-40: GAT CTG CTG CAG TTA GCA TTT CGG CGC CTG
         AGC ATC ATT TAG
``` for the N3A/N6D-mutation (SEQ ID NOs: 28-29).

PCR reaction tubes containing: 0.5 µl template pGEM ZN23T [500 ng/µl], 5 pmol of each primer (Interactiva, Thermo Hybaid GmbH, Ulm, Germany), 5 µl of dNTP-mix ([10 mM], Applied Biosystems, CA, USA), 5 µl of PCR-buffer 10× (Applied Biosystems, CA, USA), 0.1 µl of AMPLITAQ™ DNA polymerase ([5 U/µl], Applied Biosystems, CA, USA) and sterile water to a final volume of 50 µl. The PCR-program consisted of 2 min at 94° C. followed by 30 cycles of 15 sec at 96° C., 15 sec at 50° C., 1 min at 72° C. and concluded with an additional min at 72° C. The PCR reactions were performed on GENEAMP® PCR System 9700 (Applied Biosystems, CA, USA).

The PCR-product was analysed on 1% agarose gel and, after confirming an obtained product of correct size, purified with QIAQUICK® PCR purification kit (QIAGEN GmbH, Hilden, Germany).

The PCR-products were cleaved according to Sambrook (Sambrook et al.) with the restriction enzymes AccI and PstI (New England Biolabs, NEB, MA, USA). The cleavage products were analysed on agarose gel and purified from the agarose with QIAQUICK® Gel Extraction Kit (QIAGEN GmbH, Hilden, Germany) prior to ligation. The fragments were ligated into a vector denoted "pTrp-protA-stab-(multi9)", already cleaved with the enzymes AccI and PstI and purified, by adding T4 DNA ligase and ligation buffer (MBI Fermentas, Lithuania), and subsequently transformed into RRIΔM15-cells (ATCC, MA, USA). The constructs were given the names pAY87 (Z(N23T/K4G)-Cys), pAY89 (Z(N23T/N3A)-Cys) and pAY91 (Z(N23T/N3A/N6D)-Cys), respectively.

A MEGABACE™ 1000 DNA Sequencing System (Amersham Biosciences, Uppsala, Sweden) was used to verify correct sequences of inserted fragments. MEGABACE™ terminator chemistry (Amersham Biosciences, Uppsala, Sweden) was utilised according to the supplier's recommendations in a cycle sequencing protocol based on the dideoxy method (Sanger et al., 1977).

Example 4(b)

Non-Cysteine-Containing Monomer Construction

As template for the construction, a plasmid denoted "pTrp (—N)ZN23T-Cys", was used. This plasmid already contained the gene with the N23T-mutation.

A PCR-reaction was performed with this plasmid as template and the two oligonucleotides

```
AFFI-63: TTT TTT GTA GAC AAC GGA TTC AAC AAA GAA C

GRTO-41: GAT CTC GTC TAC TTT CGG CGC CTG AGC ATC
         ATT TAG
``` for the K4G-mutation (SEQ ID NOs: 30-31),

```
AFFI-64: TTT TTT GTA GAC GCC AAA TTC AAC AAA GAA C

GRTO-41: GAT CTC GTC TAC TTT CGG CGC CTG AGC ATC
         ATT TAG
``` for the N3A-mutation (SEQ ID NOs: 32-33),

```
AFFI-65: TTT TTT GTA GAC AAC GGA TTC AAC AAA GAA C

GRTO-41: GAT CTC GTC TAC TTT CGG CGC CTG AGC ATC
         ATT TAG
``` and for the N3A/N6D-mutation (SEQ ID NOs: 34-35).

PCR-reaction tubes containing: 0.5 µl template pTrp(—N) ZN23T-Cys [500 ng/µl], 5 pmol of each primer (Interactiva, Thermo Hybaid GmbH, Ulm, Germany), 5 µl of dNTP-mix (10 mM, Applied Biosystems, CA, USA), 5 µl of PCR-buffer 10× (Applied Biosystems, CA, USA), 0.1 µl of AMPLITAQ™ DNA polymerase ([5 U/µl], Applied Biosystems, CA, USA) and sterile water to a final volume of 50 µl. The PCR-program consisted of 2 min at 94° C. followed by 30 cycles of 15 sec at 96° C., 15 sec at 50° C., 1 min at 72° C. and concluded with an additional min at 72° C. The PCR reactions were performed on GENEAMP® PCR System 9700 (Applied Biosystems, CA, USA).

The PCR-products were directly TA-cloned into the vector pGEM according to the manufacturer's instructions (Promega, Wis., USA) and subsequently transformed into RRIΔM15-cells (ATCC, MA, USA). The constructs were given the names pAY86 (Z(N23T/K4G), pAY88 (Z(N23T/N3A) and pAY90 (Z(N23T/N3A/N6D) respectively.

A MEGABACE™ 1000 DNA Sequencing System (Amersham Biosciences, Uppsala, Sweden) was used to verify correct sequences of inserted fragments. MEGABACE™ terminator chemistry (Amersham Biosciences, Uppsala, Sweden) was utilised according to the supplier's recommendations in a cycle sequencing protocol based on the dideoxy method (Sanger et al., 1977).

Example 5

Construction of the Gene Encoding Monomers and Oligomers with a C-Terminal Cysteine in pTrp-Vector All of the above described plasmids pAY 86 to pAY91 (a total of six plasmids) were cleaved with the restriction enzyme AccI. This resulted in releasing the Z-mutants completely from the pAY86-, pAY88- and pAY90-vectors and a single opening at the 3'-end of the gene in the pAY87-, pAY89- and pAY91-vectors.

The cleaved vectors were treated with Calf Intestine Alkaline Phosphatase (CIAP, MBI Fermentas, Lithuania) according to the manufacturer's recommendations. This step was performed to dephosphorylate the 5'-ends to avoid self-ligation of the vectors.

The released Z-mutant-fragments were analysed on agarose gel and subsequently purified from the agarose before the fragments was ligated into the opened vectors according to the following:

fragment from pAY86 to pAY87 fragment from pAY88 to pAY89 fragment from pAY90 to pAY91

For the ligation reactions, different proportions of fragment versus vector were mixed and the result was that a range of different multimers, as expected, ranging from dimers to pentamers was obtained.

The different multimers were transformed into RRIΔM15-cells (ATCC, MA, USA) and the correct sequences were verified by analysis on a sequencing equipment at the Royal Institute of Technology as described above. The newly constructed plasmids were denoted as shown in the table below:

TABLE 2

Summary of constructed plasmids

| Plasmid no. pAY | Expressed protein from construct |
|---|---|
| 86 | Z(N23T/K4G) |
| 87 | Z(N23T/K4G)-Cys |
| 88 | Z(N23T/N3A) |
| 89 | Z(N23T/N3A)-Cys |
| 90 | Z(N23T/N3A/N6D) |
| 91 | Z(N23T/N3A/N6D)-Cys |
| 92 | Z(N23T/K4G)dimer-Cys |
| 93 | Z(N23T/N3A)dimer-Cys |
| 94 | Z(N23T/N3A/N6D)dimer-Cys |
| 95 | Z(N23T/K4G)trimer-Cys |
| 96 | Z(N23T/N3A)trimer-Cys |
| 97 | Z(N23T/N3A/N6D)trimer-Cys |
| 98 | Z(N23T/K4G)tetramer-Cys |
| 99 | Z(N23T/N3A)tetramer-Cys |
| 100 | Z(N23T/N3A/N6D)tetramer-Cys |
| 101 | Z(N23T/K4G)pentamer-Cys |
| 102 | Z(N23T/N3A)pentamer-Cys |
| 103 | Z(N23T/N3A/N6D)pentamer-Cys |

The above described plasmid vectors, except pAY86, pAY88 and pAY90 have Trp promoter, Trp leader sequence and a gene for kanamycin (Km) resistance. pAY86, pAY88 and pAY90 have a gene for ampicillin resistance instead.

Example 6

Construction of Genes Encoding Monomers and Oligomers with a C-Terminal Cysteine in pK4-Vector The genes encoding the proteins as summarised in Table 2 were to be transferred to a vector containing SPA promoter and signal sequence. To enable this procedure, an adapter containing the cleavage site for the restriction enzyme KpnI (New England Biolabs, NEB, MA, USA) was to be constructed. The adapter was constructed by the two oligonucleotides (Interactiva, Thermo Hybaid GmbH, Ulm, Germany)

The plasmid pAY104 (pK4-cys-ABDstabdimer) was cleaved with FspI and PstI (New England Biolabs, NEB, MA, USA). The vector was purified on agarose gel and the released fragment was removed and the remaining vector was purified from the agarose with QIAQUICK® Gel Extraction Kit (QIAGEN GmbH, Hilden, Germany). The two oligomers AFFI-88 and AFFI-89 were mixed in ligation buffer (MBI Fermentas, Lithuania) and heated to 50° C. and the mixture was allowed to cool to room temperature where after the cleaved plasmid vector was added together with T4 DNA ligase (MBI Fermentas, Lithuania). After the ligation reaction, the product was transformed into RRIΔM15-cells and the correct sequence was verified as described above. The resulting plasmid was denoted pAY128.

The plasmid pAY128 was then cleaved with the restriction enzymes KpnI and PstI and the cleaved vector was analysed on agarose gel and subsequently purified from the agarose with QIAQUICK® Gel Extraction Kit (QIAGEN GmbH, Hilden, Germany). The fragments expressing the two mutated Z-genes Z(N23T/N3A) and Z(N23T/N3A/N6A) from pAY86 to pAY103 were cleaved with KpnI and PstI (New England Biolabs, NEB, MA, USA), separated and purified after agarose gel separation. The different fragments were ligated into the cleaved vector originating from pAY128 and the resulting plasmids were, after verifying correct sequences, denoted pAY107 to pAY116 as summarised in Table 3.

TABLE 3

Summary of constructed plasmids with SPA promoter and signal sequence.

| Plasmid no. pAY | Expressed protein from construct |
|---|---|
| 107 | Z(N23T/N3A)-Cys |
| 108 | Z(N23T/N3A/N6D)-Cys |
| 109 | Z(N23T/N3A)dimer-Cys |
| 110 | Z(N23T/N3A/N6D)dimer-Cys |
| 111 | Z(N23T/N3A)trimer-Cys |
| 112 | Z(N23T/N3A/N6D)trimer-Cys |
| 113 | Z(N23T/N3A)tetramer-Cys |
| 114 | Z(N23T/N3A/N6D)tetramer-Cys |
| 115 | Z(N23T/N3A)pentamer-Cys |
| 116 | Z(N23T/N3A/N6D)pentamer-Cys |

Example 7

Construction of Genes Encoding a Part of the E-Gene (E') from Protein a N-Terminally Fused to Monomers and Oligomers with a C-Terminal Cysteine in pK4-Vector The genes encoding the proteins, as summarised in Table 2, were transferred to a vector containing the SPA promoter and signal sequence and a part of the gene encoding the E-region of protein A (E'). It has earlier been shown that an addition of the N-terminal IgG-binding part of the mature protein A (region E), or parts thereof, may increase correct processing and also facilitate secretion of the gene product to the surrounding culture medium (Abrahmsén et al., 1985). An adapter containing the cleavage site for the restriction enzyme KpnI and a part of region E from protein A (E') was constructed by the two oligonucleotides (Interactiva, Thermo Hybaid GmbH, Ulm, Germany)

The plasmid pAY104 (pK4-cys-ABDstabdimer) was cleaved with FspI and PstI (New England Biolabs, NEB, MA, USA). The vector was purified on agarose gel and the released fragment was removed and the remaining vector was purified from the agarose with QIAQUICK® Gel Extraction Kit (QIAGEN GmbH, Hilden, Germany). The two oligonucleotides were mixed in ligation buffer and heated to 75° C. and the mixture was allowed to cool to room temperature where after the cleaved plasmid vector was added, together with T4 DNA ligase (MBI Fermentas, Lithuania). After the ligation reaction the product was transformed into RRIΔM15-cells and the correct sequence was verified as described above. The resulting plasmid was denoted pAY129.

The plasmid pAY129 was then cleaved with the restriction enzymes KpnI and PstI and the cleaved vector was analysed on agarose gel and subsequently purified from the agarose with QIAQUICK® Gel Extraction Kit (QIAGEN GmbH, Hilden, Germany). The fragments expressing the two mutated Z-genes Z(N23T/N3A) and Z(N23T/N3A/N6A) from pAY86 to pAY103 were cleaved with KpnI and PstI, separated and purified after agarose gel separation. The different fragments were ligated into the cleaved vector originating from pAY129 and the resulting plasmids were, after verifying correct sequences, denoted pAY118 to pAY127 as summarised in Table 4.

TABLE 4

Summary of constructed plasmids with SPA promoter and signal sequence and a part of region E from protein A-E'.

| Plasmid no. pAY | Expressed protein from construct |
|---|---|
| 118 | E'-Z(N23T/N3A)-Cys |
| 119 | E'-Z(N23T/N3A/N6D)-Cys |
| 120 | E'-Z(N23T/N3A)dimer-Cys |
| 121 | E'-Z(N23T/N3A/N6D)dimer-Cys |
| 122 | E'-Z(N23T/N3A)trimer-Cys |
| 123 | E'-Z(N23T/N3A/N6D)trimer-Cys |
| 124 | E'-Z(N23T/N3A)tetramer-Cys |
| 125 | E'-Z(N23T/N3A/N6D)tetramer-Cys |
| 126 | E'-Z(N23T/N3A)pentamer-Cys |
| 127 | E'-Z(N23T/N3A/N6D)pentamer-Cys |

Example 8

Stability Towards Alkaline Conditions

To evaluate the stability of the proteins towards alkaline conditions, four different proteins were tested in an environment of high pH. The different proteins were Z(N23T)dimer-Cys, Z(N23T/K4G)dimer-Cys, Z(N23T/N3A)dimer-Cys and Z(N23 T/N3A/N6D)dimer-Cys.

(Z(N23T)dimer-Cys), (Z(N23T/N3A)dimer-Cys), (Z(N23 T/N3A/N6D)dimer-Cys) and (Z(N23T/K4G)dimer-Cys) were cultivated in fermenters. The harvested media were purified and coupled to HF Agarose (Amersham Biosciences, Uppsala, Sweden) using standard methods before the alkaline tests. The HF agarose-coupled proteins were denoted as follows Z(N23T)dimer-Cys U631049
Z(N23T/K4G)dimer-Cys U631079
Z(N23T/N3A)dimer-Cys U631064
Z(N23T/N3A/N6D)dimer-Cys U631063

The matrices were packed in columns (HR 5/2, Amersham Biosciences, Uppsala, Sweden) to a final volume ranging from 0.1 to 0.3 ml. The purification equipment used was an ÄKTA™ explorer 10 (Amersham Biosciences, Uppsala, Sweden) with a UV sample flow cell with a path length of 2 mm (Amersham Biosciences, Uppsala, Sweden).

The buffers used contained

Running buffer: 25 mM Tris-HCl, 1 mM EDTA, 200 mM NaCl, 0.05% Tween 20, 5 mM ammonium acetate, pH 8.0

Elution buffer: 0.2 M acetic acid (HAc), pH 3.1
Cleaning-In-Place (CIP) buffer: 0.5 M NaOH
A typical chromatographic run cycle consisted of
Equilibrium of the column with running buffer
Sample application of 10 mg polyclonal human IgG (hIgG) at 0.2 ml/min
Extensive washing-out of unbound proteins
Elution at 1.0 ml/min with elution buffer
Re-equilibration with running buffer
Cleaning-In-Place (CIP) with CIP-buffer with a contact time between column matrix and 0.5 M NaOH of 1 hour
Re-equilibration with running buffer The amount of hIgG loaded at each run was well above the total dynamic binding capacity of the column since the breakthrough of unbound protein was considerable when loading the sample onto the columns in all cases.

After one cycle, including the steps above, a new cycle was started which again included one hour of exposure of 0.5 M sodium hydroxide. To measure the decrease of the dynamic binding capacity of the column the peak area of the eluted peak was compared with the original peak area of the eluted peak when the matrix had not been exposed to the sodium hydroxide. Setting the original peak area as 100% of binding capacity the decrease of the binding capacity of hIgG was observed. The peak area was calculated with the UNICORN™ software accompanying the purification system. Each cycle was repeated 21 times resulting in a total exposure time between the matrix and the sodium hydroxide of 20 hours for each different matrix. The normalised peak areas were visualised in a graph as can be seen below (FIG. 16). All 21 cycles were repeated for each mutant.

Both Z(N23T/N3A/N6D)dimer-Cys and Z(N23T/N3A) dimer-Cys showed improved stability against alkaline conditions compared to the originally produced Z(N23T)dimer-Cys.

Example 9

Stability Towards Protease

The purpose of this example was to investigate whether a separation matrix comprising alkaline-stable protein-based ligands (MABSELECT™ SURE™) according to the present invention is more resistant to protease activity than a Protein A separation matrix according to the prior art, herein exemplified by MABSELECT™ matrix (GE Healthcare Bio-Sciences), which comprises protein A ligands expressed in *E. coli* coupled to an agarose. The experiment was designed using fluorescent labelled ligands. Each of the two ligands was labelled with different fluors and equal amount of respectively ligand was pooled and subjected to two different concentrations of chymotrypsin (FIG. 17) or a cell lysate from CHO cells (FIG. 18).

Samples were taken from each of the vials at different times, each of the samples were loaded on an SDS-PAGE. After the separation the gel was scanned using a TYPHOON™ and evaluated using the software IMAGEQUANT™.

Materials:

NAP™-10 columns; GE Healthcare Bio-Sciences.
PHASTGEL™ homogenous 20 Healthcare Bio-Sciences.
PHASTGEL™ SDS buffer strips Healthcare Bio-Sciences.
Sample buffer for SDS-PAGE: 10 mM Tris-HCl, 1 mM EDTA, 2.5% SDS and
50 mM DTT pH 8.0
20 mM NaHCO$_3$ pH 8.3
CYDYE™ DIGE Fluor CY™3 GE Healthcare Bio-Sciences
CYDYE™ DIGE Fluor CY™5 GE Healthcare Bio-Sciences
1M sodium acetate pH 3.5
2M Tris
PBS, Sigma code P-4417 prepared according to the manufacturers instructions.
Chymotrypsin, TLCK treated 81 U/mg, Sigma Alkaline-stabilized protein-based ligand diluted to 1.5 mg/mL with deionized water. MABSELECT™ ligand diluted to 1.5 mg/mL with deionized water.

Methods:

Fluorescent Labelling:
1. Equilibrate two NAP-10 columns with 15 ml 20 mM NaHCO$_3$ pH 8.3, apply 1 mL 1.5 mg/mL of the ligand solutions and after the sample completely has entered the gel bed eluted by adding 1.5 mL equilibration solution and collect the eluate.
2. Label 125 μL of the eluates, about 125 μg, with the desired fluore by adding 1 μL of the desired dyes stock solution, prepared according to manufacturers recommendation. The reaction was allowed to proceed for 30 minutes at 8° C. in the dark.

Experimental:

8 μL of the CY™3 labelled MABSELECT™ ligand was mixed with 8 μL CY™5 labelled alkaline-stabilized protein-based ligand together with 0, 0.1 or 0.5 μg chymotrypsin and the volume was adjusted to 100 μL with PBS. The vials containing the mixtures were wrapped in aluminum foil at placed at 37° C.

A 10 μL sample was taken immediately and mixed with 10 μL sample buffer. The mixture was heat treated at 95° C. for 3-5 minutes and left to cool at room temperature.

At 15, 30 and 60 minutes new samples were taken and treated as the previous sample taken zero minutes.

The samples were separated on a SDS-PAGE.

The SDS-PAGE gels were than scanned using a TYPHOON™ scanner and the obtained images were analysed using IMAGEQUANT™ both from GE Healthcare Bio-Sciences.

Results (Example 9)

FIG. 17 shows how already after 15 minutes incubation, a degradation of MABSELECT™ ligand can be seen while the MABSELECT™ SURE™ ligand stays intact when incubated with 5 μg/mL. After 30 minutes degradation becomes obvious for the 1 μg/mL chymotrypsin treated MABSELECT™ ligand. When incubated 60 minutes with 5 μg/mL no intact MABSELECT™ ligand can be detected. For MABSELECT™ SURE™ ligand no degradation can be observed for any of the tested conditions. In conclusion, MABSELECT™ SURE™ ligand stays intact for one hour at 37° C. treated with 5 μg/mL chymotrypsin, whereas MABSELECT™ starts to degrade already after 15 minutes and becomes completely degraded after 60 minutes at the same conditions.

FIG. 18 shows how an obvious degradation of the MABSELECT™ ligand when incubated in CHO cell lysate at pH 5 for 18 hours at 37° C. can be seen. The MABSELECT™ SURE™ ligand stays intact when incubated with the same conditions. In conclusion, the MABSELECT™ SURE™ ligand is more protease stable than the MABSELECT™ ligand even in a CHO cell lysate.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. In a method of separating antibodies from proteases, which method comprises
   (a) contacting a liquid comprising antibodies and protease(s) with a separation matrix to adsorb antibodies;
   (b) separating the liquid comprising protease(s) from the matrix; and optionally,
   (c) releasing the antibodies from the matrix by adding an eluent;
   the improvement being that the separation matrix comprises alkali-stable protein A-based ligands which provide increased resistance of said alkali-stable protein A-based ligands to protease degradation, wherein each of said alkali-stable protein A-based ligands is represented by SEQ ID NO: 1 or SEQ ID NO: 2, with one or two asparagine residues mutated, and the mutation is N23T; N23T, N43E; N28A; N6A; N11S; N11S, N23T; or N6A, N23T, further wherein said antibodies being separated are selected from the group consisting of IgG, IgA and IgM.

2. The method of claim 1, wherein the alkali-stable protein A-based ligands comprise at least one B domain of Protein A (SEQ ID NO: 1) in which at least one asparagine residue has been mutated as defined in claim 1.

3. The method of claim 1, wherein the alkali-stable protein A-based ligands comprise at least one Protein Z domain of SEQ ID NO: 2 in which at least one asparagine residue has been mutated as defined in claim 1.

4. The method of claim 1, wherein the alkali-stable protein A-based ligands are multimers of two or more mutated Protein Z domains of SEQ ID NO: 2, wherein in each domain at least one asparagine residue has been mutated as defined in claim 1.

5. The method of claim 1, wherein the antibodies are monoclonal antibodies.

* * * * *

SEQUENCE LISTING

<160> NUMBER OF SEQ ID NOS: 35

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
 1               5                  10                  15

Leu His Leu Pro Asn Leu Asn Glu Glu Gln Arg Asn Gly Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 2
<211> LENGTH: 58
<212> TYPE: PRT
<213> ORGANISM: Staphylococcus aureus
<220> FEATURE:
<221> NAME/KEY: MUTAGEN
<222> LOCATION: (29)

<400> SEQUENCE: 2

Val Asp Asn Lys Phe Asn Lys Glu Gln Gln Asn Ala Phe Tyr Glu Ile
 1               5                  10                  15

Leu His Leu Pro Asn Leu Asn Glu Glu Gln Arg Asn Ala Phe Ile Gln
             20                  25                  30

Ser Leu Lys Asp Asp Pro Ser Gln Ser Ala Asn Leu Leu Ala Glu Ala

```
                 35                  40                  45

Lys Lys Leu Asn Asp Ala Gln Ala Pro Lys
     50                  55

<210> SEQ ID NO 3
<211> LENGTH: 58
<212> TYPE: PRT
<213> ORGANISM: Staphylococcus aureus
<220> FEATURE:
<221> NAME/KEY: MUTAGEN
<222> LOCATION: (29)
<220> FEATURE:
<221> NAME/KEY: MUTAGEN
<222> LOCATION: (30)

<400> SEQUENCE: 3

Val Asp Asn Lys Phe Asn Lys Glu Gln Gln Asn Ala Phe Tyr Glu Ile
 1               5                  10                  15

Leu His Leu Pro Asn Leu Asn Glu Glu Gln Arg Asn Ala Ala Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 4
<211> LENGTH: 58
<212> TYPE: PRT
<213> ORGANISM: Staphylococcus aureus
<220> FEATURE:
<221> NAME/KEY: MUTAGEN
<222> LOCATION: (23)

<400> SEQUENCE: 4

Val Asp Asn Lys Phe Asn Lys Glu Gln Gln Asn Ala Phe Tyr Glu Ile
 1               5                  10                  15

Leu His Leu Pro Asn Leu Thr Glu Glu Gln Arg Asn Gly Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 5
<211> LENGTH: 33
<212> TYPE: PRT
<213> ORGANISM: Staphylococcus aureus

<400> SEQUENCE: 5

Ala Asn Asn Phe Asn Lys Glu Gln Asn Met Ala Phe Tyr Glu Ile Leu
 1               5                  10                  15

His Leu Pro Asn Leu Asn Glu Glu Ser Arg Asn Gly Glu Ser Gln Ser
             20                  25                  30

Leu

<210> SEQ ID NO 6
<211> LENGTH: 31
<212> TYPE: PRT
<213> ORGANISM: Staphylococcus aureus

<400> SEQUENCE: 6

Ala Asn Lys Phe Asn Lys Glu Gln Gln Asn Thr Phe Tyr Glu Ile Leu
```

```
                1               5                  10                 15
His Leu Pro Val Leu Lys Glu Ile Gln Arg Asn Gly Phe Ile Gln
                        20                  25                  30
```

<210> SEQ ID NO 7
<211> LENGTH: 38
<212> TYPE: PRT
<213> ORGANISM: Staphylococcus aureus

<400> SEQUENCE: 7

```
Ala Ala Gln Gln Lys Asn Asn Asp Glu Ser Gln Asn Ala Asn Met Glu
 1               5                  10                  15
Ile Leu His Leu Pro Asn Leu Asn Glu Glu Gln Arg Asn Gly Phe Ile
                20                  25                  30
Gln Ser Glu Ser Asp Ser
                35
```

<210> SEQ ID NO 8
<211> LENGTH: 38
<212> TYPE: PRT
<213> ORGANISM: Staphylococcus aureus

<400> SEQUENCE: 8

```
Ala Gln His Asp Glu Ala Glu Gln Gln Val Phe Asn Met Ile Leu
 1               5                  10                  15
His Ala Asp Asn Leu Asn Glu Glu Gln Arg Asn Gly Val Ile Gln Ser
                20                  25                  30
Gln Lys Asp Ser Pro Ser
                35
```

<210> SEQ ID NO 9
<211> LENGTH: 31
<212> TYPE: PRT
<213> ORGANISM: Staphylococcus aureus

<400> SEQUENCE: 9

```
Val Asp Asn Lys Phe Asn Lys Glu Gln Gln Asn Ala Phe Tyr Ala Ile
 1               5                  10                  15
Leu His Leu Pro Asn Leu Asn Glu Glu Gln Arg Asn Gly Phe Ile
                20                  25                  30
```

<210> SEQ ID NO 10
<211> LENGTH: 72
<212> TYPE: PRT
<213> ORGANISM: Staphylococcus aureus

<400> SEQUENCE: 10

```
Met Lys Ala Ile Phe Val Leu Asn Ala Gln His Asp Glu Ala Val Asp
 1               5                  10                  15
Asn Lys Phe Asn Lys Glu Gln Gln Asn Ala Phe Tyr Glu Ile Leu His
                20                  25                  30
Leu Pro Asn Leu Asn Glu Glu Gln Arg Asn Ala Phe Ile Gln Ser Leu
            35                  40                  45
Lys Asp Asp Pro Ser Gln Ser Ala Asn Leu Leu Ala Glu Ala Lys Lys
     50                  55                  60
Leu Asn Asp Ala Gln Ala Pro Lys
 65                  70
```

<210> SEQ ID NO 11
<211> LENGTH: 36

<212> TYPE: PRT
<213> ORGANISM: Staphylococcus aureus

<400> SEQUENCE: 11

Gln Gln Asn Gly Thr Ala Leu His Leu Pro Asn Leu Asn Glu Glu Gln
1               5                   10                  15

Arg Asn Ala Phe Ile Gln Ser Leu Lys Asp Asp Pro Ser Gln Ser Ala
            20                  25                  30

Asn Leu Leu Ala
        35

<210> SEQ ID NO 12
<211> LENGTH: 198
<212> TYPE: DNA
<213> ORGANISM: Artificial Sequence
<220> FEATURE:
<223> OTHER INFORMATION: Description of Artificial Sequence: synthetic
      DNA construct
<220> FEATURE:
<221> NAME/KEY: CDS
<222> LOCATION: (1)..(186)

<400> SEQUENCE: 12 ctg ggt acc gta gac gcc aaa ttc gac aaa gaa caa caa aac gcg ttc      48
Leu Gly Thr Val Asp Ala Lys Phe Asp Lys Glu Gln Gln Asn Ala Phe
1               5                   10                  15 tat gag atc tta cat tta cct aac tta act gaa gaa caa cga aac gcc      96
Tyr Glu Ile Leu His Leu Pro Asn Leu Thr Glu Glu Gln Arg Asn Ala
            20                  25                  30 ttc atc caa agt tta aaa gat gac cca agc caa agc gct aac ctt tta    144
Phe Ile Gln Ser Leu Lys Asp Asp Pro Ser Gln Ser Ala Asn Leu Leu
        35                  40                  45 gca gaa gct aaa aag cta aat gat gct cag gcg ccg aaa tgc              186
Ala Glu Ala Lys Lys Leu Asn Asp Ala Gln Ala Pro Lys Cys
    50                  55                  60 taactgcagc tc                                                       198

<210> SEQ ID NO 13
<211> LENGTH: 62
<212> TYPE: PRT
<213> ORGANISM: Artificial Sequence
<220> FEATURE:
<223> OTHER INFORMATION: Description of Artificial Sequence: synthetic
      peptide encoded by DNA construct

<400> SEQUENCE: 13

Leu Gly Thr Val Asp Ala Lys Phe Asp Lys Glu Gln Gln Asn Ala Phe
1               5                   10                  15

Tyr Glu Ile Leu His Leu Pro Asn Leu Thr Glu Glu Gln Arg Asn Ala
            20                  25                  30

Phe Ile Gln Ser Leu Lys Asp Asp Pro Ser Gln Ser Ala Asn Leu Leu
        35                  40                  45

Ala Glu Ala Lys Lys Leu Asn Asp Ala Gln Ala Pro Lys Cys
    50                  55                  60

<210> SEQ ID NO 14
<211> LENGTH: 192
<212> TYPE: DNA
<213> ORGANISM: Artificial Sequence
<220> FEATURE:
<223> OTHER INFORMATION: Description of Artificial Sequence: synthetic
      DNA construct
<220> FEATURE:
<221> NAME/KEY: CDS -continued

<222> LOCATION: (1)..(180)

<400> SEQUENCE: 14

| | | | | | | | | | | | | | | | |
|---|---|---|---|---|---|---|---|---|---|---|---|---|---|---|---|
| ttt | ttt | gta | gac | gcc | aaa | ttc | gac | aaa | gaa | caa | caa | aac | gcg | ttc | tat | 48 |
| Phe | Phe | Val | Asp | Ala | Lys | Phe | Asp | Lys | Glu | Gln | Gln | Asn | Ala | Phe | Tyr |
| 1 | | | | 5 | | | | | 10 | | | | | 15 |

| gag | atc | tta | cat | tta | cct | aac | tta | act | gaa | gaa | caa | cga | aac | gcc | ttc | 96 |
|---|---|---|---|---|---|---|---|---|---|---|---|---|---|---|---|---|
| Glu | Ile | Leu | His | Leu | Pro | Asn | Leu | Thr | Glu | Glu | Gln | Arg | Asn | Ala | Phe |
| | | | 20 | | | | | 25 | | | | | 30 |

| atc | caa | agt | tta | aaa | gat | gac | cca | agc | caa | agc | gct | aac | ctt | tta | gca | 144 |
|---|---|---|---|---|---|---|---|---|---|---|---|---|---|---|---|---|
| Ile | Gln | Ser | Leu | Lys | Asp | Asp | Pro | Ser | Gln | Ser | Ala | Asn | Leu | Leu | Ala |
| | | 35 | | | | | 40 | | | | | 45 |

| gaa | gct | aaa | aag | cta | aat | gat | gct | cag | gcg | ccg | aaa | gtagacaaaa | aa | 192 |
|---|---|---|---|---|---|---|---|---|---|---|---|---|---|---|
| Glu | Ala | Lys | Lys | Leu | Asn | Asp | Ala | Gln | Ala | Pro | Lys |
| 50 | | | | | 55 | | | | | 60 |

<210> SEQ ID NO 15
<211> LENGTH: 60
<212> TYPE: PRT
<213> ORGANISM: Artificial Sequence
<220> FEATURE:
<223> OTHER INFORMATION: Description of Artificial Sequence: synthetic
      peptide encoded by DNA construct

<400> SEQUENCE: 15

Phe Phe Val Asp Ala Lys Phe Asp Lys Glu Gln Gln Asn Ala Phe Tyr
1               5                   10                  15

Glu Ile Leu His Leu Pro Asn Leu Thr Glu Glu Gln Arg Asn Ala Phe
            20                  25                  30

Ile Gln Ser Leu Lys Asp Asp Pro Ser Gln Ser Ala Asn Leu Leu Ala
        35                  40                  45

Glu Ala Lys Lys Leu Asn Asp Ala Gln Ala Pro Lys
    50                  55                  60

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: synthetic
      DNA construct

<400> SEQUENCE: 16
gcagggtacc ctgca                                                    15

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: synthetic
      DNA construct

<400> SEQUENCE: 17
gggtaccctg c                                                        11

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: synthetic
      DNA construct

<400> SEQUENCE: 18

```
gcaaatgctg cgcagggtac cctgcagggg ggggggggaa                                    40
```

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: synthetic
      DNA construct

<400> SEQUENCE: 19

```
gcaacacgat gaagccggta ccctgca                                                  27
```

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: synthetic
      DNA construct

<400> SEQUENCE: 20

```
gggtaccggc ttcatcgtgt tgc                                                      23
```

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: synthetic
      DNA construct

<400> SEQUENCE: 21

```
gcaaatgctg cgcaacacga tgaagccggt accctgcagg gggggggggg                         50
```

<210> SEQ ID NO 22
<211> LENGTH: 137
<212> TYPE: PRT
<213> ORGANISM: Artificial Sequence
<220> FEATURE:
<223> OTHER INFORMATION: Description of Artificial Sequence: synthetic
      peptide multimer

<400> SEQUENCE: 22

```
Val Asp Ala Lys Phe Asn Val Asp Asn Lys Phe Asn Lys Glu Gln
 1               5                  10                  15

Gln Asn Ala Phe Tyr Glu Ile Leu His Leu Pro Asn Leu Thr Glu
             20                  25                  30

Glu Gln Arg Asn Ala Phe Ile Gln Ser Leu Lys Asp Asp Pro Ser
         35                  40                  45

Gln Ser Ala Asn Leu Leu Ala Glu Ala Lys Lys Leu Asn Asp Ala
     50                  55                  60

Gln Ala Pro Lys Gln Ala Pro Lys Val Asp Ala Lys Phe Asn Val
 65                  70                  75

Asp Asn Lys Phe Asn Lys Glu Gln Gln Asn Ala Phe Tyr Glu Ile
                 80                  85                  90

Leu His Leu Pro Asn Leu Thr Glu Glu Gln Arg Asn Ala Phe Ile
             95                 100                 105

Gln Ser Leu Lys Asp Asp Pro Ser Gln Ser Ala Asn Leu Leu Ala
         110                 115                 120

Glu Ala Lys Lys Leu Asn Asp Ala Gln Ala Pro Lys Gln Ala Pro
     125                 130                 135
```

```
<210> SEQ ID NO 23
<211> LENGTH: 195
<212> TYPE: PRT
<213> ORGANISM: Artificial Sequence
<220> FEATURE:
<223> OTHER INFORMATION: Description of Artificial Sequence: synthetic
      peptide multimer

<400> SEQUENCE: 23

Val Asp Ala Lys Phe Asp Val Asp Asn Lys Phe Asn Lys Glu Gln
 1               5                  10                  15

Gln Asn Ala Phe Tyr Glu Ile Leu His Leu Pro Asn Leu Thr Glu
            20                  25                  30

Glu Gln Arg Asn Ala Phe Ile Gln Ser Leu Lys Asp Asp Pro Ser
        35                  40                  45

Gln Ser Ala Asn Leu Leu Ala Glu Ala Lys Lys Leu Asn Asp Ala
    50                  55                  60

Gln Ala Pro Lys Gln Ala Pro Lys Val Asp Ala Lys Phe Asp Val
65                  70                  75

Asp Asn Lys Phe Asn Lys Glu Gln Gln Asn Ala Phe Tyr Glu Ile
                80                  85                  90

Leu His Leu Pro Asn Leu Thr Glu Glu Gln Arg Asn Ala Phe Ile
                95                 100                 105

Gln Ser Leu Lys Asp Asp Pro Ser Gln Ser Ala Asn Leu Leu Ala
            110                 115                 120

Glu Ala Lys Lys Leu Asn Asp Ala Gln Ala Pro Lys Val Asp Asn
        125                 130                 135

Lys Phe Asn Lys Glu Gln Gln Asn Ala Phe Tyr Glu Ile Leu His
140                 145                 150

Leu Pro Asn Leu Asn Glu Glu Gln Arg Asn Ala Phe Ile Gln Ser
                155                 160                 165

Leu Lys Asp Asp Pro Ser Gln Ser Ala Asn Leu Leu Ala Glu Ala
            170                 175                 180

Lys Lys Leu Asn Asp Ala Gln Ala Pro Lys Gln Ala Pro Lys Cys
        185                 190                 195

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 24 tttttgtag acaacggatt caacaaagaa c                                  31

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 25
gatctgctgc agttagcatt tcggcgcctg agcatcattt ag                     42
```

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 26 tttttttgtag acgccaaatt caacaaagaa c                             31

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 27
gatctgctgc agttagcatt tcggcgcctg agcatcattt ag                  42

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 28 tttttttgtag acgccaaatt cgacaaagaa c                             31

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 29
gatctgctgc agttagcatt tcggcgcctg agcatcattt ag                  42

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 30 tttttttgtag acaacggatt caacaaagaa c                             31

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 31
gatctcgtct actttcggcg cctgagcatc atttag                         36

```
<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 32 tttttgtag acgccaaatt caacaaagaa c                                    31

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 33
gatctcgtct actttcggcg cctgagcatc atttag                              36

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 34 tttttgtag acaacggatt caacaaagaa c                                    31

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 35
gatctcgtct actttcggcg cctgagcatc atttag                              36
```